US012629681B2

(12) United States Patent
Zhu et al.

(10) Patent No.: US 12,629,681 B2
(45) Date of Patent: May 19, 2026

(54) APPARATUSES AND METHODS FOR PERFORMING MULTIPLE OMICS ANALYSIS AND PROCESSING ANALYTE MIXTURES

(71) Applicant: Battelle Memorial Institute, Richland, WA (US)

(72) Inventors: Ying Zhu, Richland, WA (US); James M. Fulcher, Pasco, WA (US); Lye Meng Markillie, Richland, WA (US); Ljiljana Paša-Tolić, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 808 days.

(21) Appl. No.: 17/954,834

(22) Filed: Sep. 28, 2022

(65) Prior Publication Data

US 2023/0113026 A1    Apr. 13, 2023

Related U.S. Application Data

(60) Provisional application No. 63/250,011, filed on Sep. 29, 2021.

(51) Int. Cl.
*B01L 3/00* (2006.01)
*C12Q 1/6869* (2018.01)
(Continued)

(52) U.S. Cl.
CPC ...... *B01L 3/502784* (2013.01); *C12Q 1/6869* (2013.01); *G01N 30/08* (2013.01);
(Continued)

(58) Field of Classification Search
CPC ..... B01L 2300/0819; B01L 2300/0822; B01L 3/502784; B01L 3/5088; B01L 3/5635;
(Continued)

(56) References Cited

U.S. PATENT DOCUMENTS

2019/0336969 A1    11/2019   Ismagilov et al.
2022/0010360 A1    1/2022   Craighead et al.
(Continued)

FOREIGN PATENT DOCUMENTS

WO    WO 2019/147714    8/2019
WO    WO 2020/113173    6/2020
(Continued)

OTHER PUBLICATIONS

Matula et al "Single-Cell Analysis Using Droplet Microfluidics". Adv. Biosys. 2020, 4, 1900188. https://doi.org/10.1002/adbi. 201900188 (Year: 2020).*
(Continued)

*Primary Examiner* — Jennifer Wecker
*Assistant Examiner* — Jonathan Bortoli
(74) *Attorney, Agent, or Firm* — Wells St. John P.S.

(57) ABSTRACT

Methods for performing multiple omics analysis in parallel are provided, the methods can include: dividing the mixture of cells or cell components into at least a first portion and a second portion; performing a first analysis on the first portion to acquire a first set of analytical data; performing a second analysis on the second portion to acquire a second set of analytical data. Methods for forming mixtures of analytes into first and second portions are also provided. The methods can include aligning the first and second plates to engage the first exposed surface with the second exposed surface, wherein the engaging is sufficient to convey at least some of the first analytes into the second solution to form a second mixture of the first analytes.

6 Claims, 30 Drawing Sheets

(51) Int. Cl.

| | |
|---|---|
| *G01N 30/06* | (2006.01) |
| *G01N 30/08* | (2006.01) |
| *G01N 30/88* | (2006.01) |

(52) U.S. Cl.
CPC ................. *G01N 2030/062* (2013.01); *G01N 2030/8831* (2013.01)

(58) Field of Classification Search
CPC .............................. C12Q 1/686; C12Q 1/6869; C12Q 2563/159; C12Q 2565/629; G01N 2030/062; G01N 2030/8831; G01N 30/08
See application file for complete search history.

(56) References Cited

U.S. PATENT DOCUMENTS

| | | | |
|---|---|---|---|
| 2023/0302451 A1* | 9/2023 | Hollfelder | ......... B01L 3/502784 |
| 2023/0304069 A1* | 9/2023 | Bell | ..................... C12Q 1/6806 |

FOREIGN PATENT DOCUMENTS

| | | |
|---|---|---|
| WO | WO 2021/022085 | 2/2021 |
| WO | PCT/US2022/045024 | 4/2024 |

OTHER PUBLICATIONS

WO PCT/US2022/045024 Search Rprt., Feb. 23, 2023, Battelle Memorial Institute.

WO PCT/US2022/045024 Writ. Opin., Feb. 23, 2023, Battelle Memorial Institute.

Haidas et al., "Parallel Sampling of Nanoliter Droplet Arrays for Noninvasive Protein Analysis in Discrete Yeast Cultivations by MALDI-MS", Analytical Chemistry, 92, 2020, United States, pp. 3810-3818.

Fulcher et al., "Parallel measurement of transcriptomes and proteomes from same single cells using nanodroplet splitting", available online at https://www.biorxiv.org/content/10.1101/2022.05.17.492137v1. full.pdf, May 18, 2022, 19 pages.

* cited by examiner

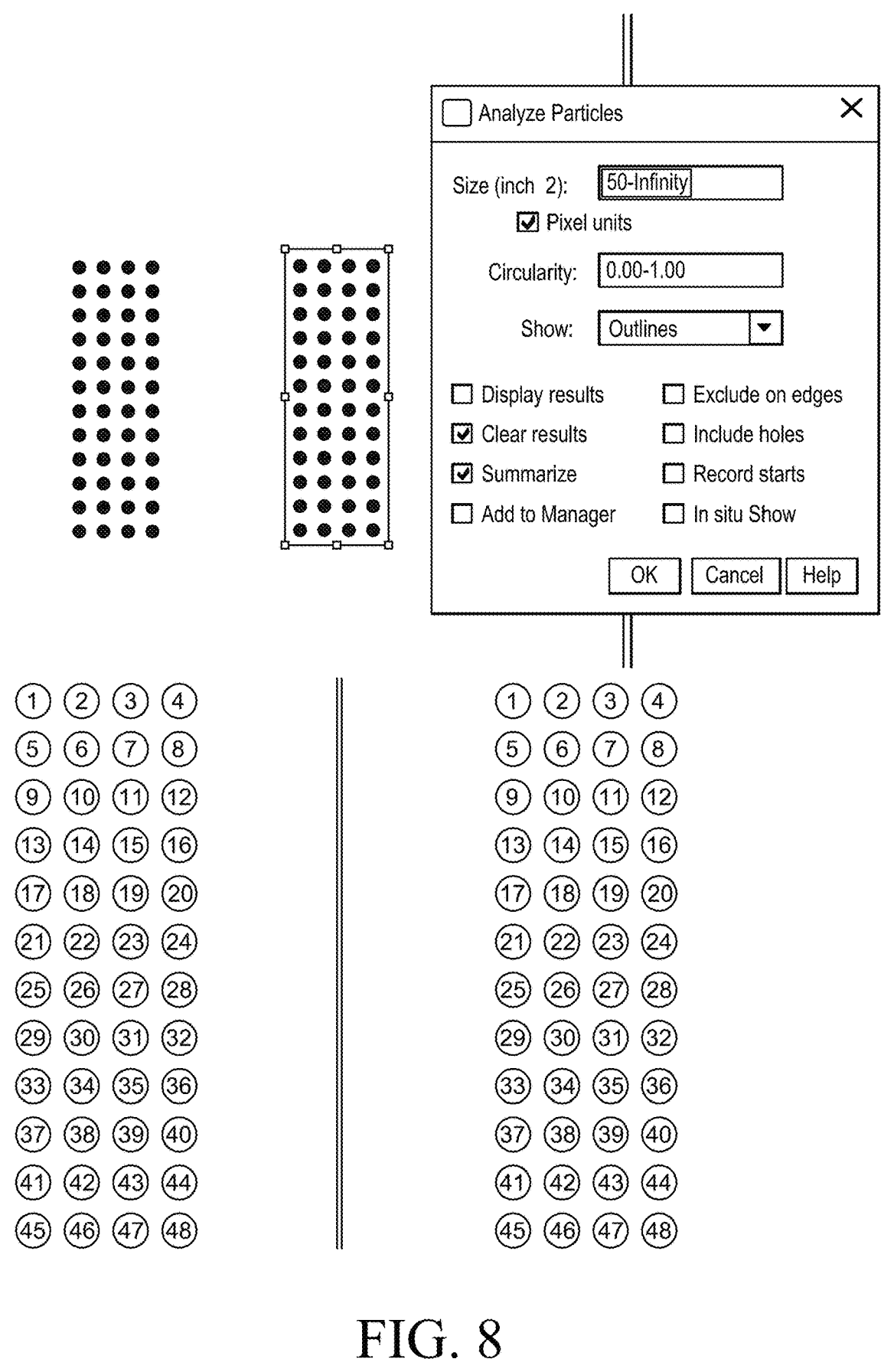

☐ Analyze Particles    ✕

Size (inch  2):    [50-Infinity]
                 ☑ Pixel units

Circularity:    [0.00-1.00]

Show:    [Outlines ▾]

☐ Display results        ☐ Exclude on edges
☑ Clear results          ☐ Include holes
☑ Summarize              ☐ Record starts
☐ Add to Manager         ☐ In situ Show

[ OK ]  [ Cancel ]  [ Help ]

FIG. 8

APPARATUSES AND METHODS FOR PERFORMING MULTIPLE OMICS ANALYSIS AND PROCESSING ANALYTE MIXTURES

CROSS REFERENCE TO RELATED APPLICATION

This application claims priority to and the benefit of U.S. Provisional Patent Application Ser. No. 63/250,011 filed Sep. 29, 2021, entitled "Method and Device for Co-Measuring Multiple Different Types of Molecules in Low Numbers of Cells", the entirety of which is incorporated by reference herein.

STATEMENT AS TO RIGHTS TO INVENTIONS MADE UNDER FEDERALLY-SPONSORED RESEARCH AND DEVELOPMENT

This invention was made with Government support under Contract DE-AC05-76RL01830 awarded by the U.S. Department of Energy. The Government has certain rights in the invention.

TECHNICAL FIELD

The present disclosure relates to apparatuses and methods for performing analysis. In particular embodiments, the present disclosure provides apparatuses and methods for performing multiple omics analysis and/or processing analyte mixtures.

BACKGROUND

The development and applications of high throughput omic technologies have transformed our understanding of cellular heterogeneities and their differential responses to internal signaling events or external perturbations. For example, single-cell whole-genome sequencing has been utilized to resolve intratumor heterogeneity and trace cell lineages during cancer progression. High throughput single-cell transcriptomics based on microfluidics technologies has increased the number of cells (>10,000) that can be measured and reveals many new and rare cell populations with critical functions. Recently-developed single-cell proteomics provides additional protein abundance and post-translational modification information as a more direct link to cell phenotype.

Despite these advances, most of the developed single-cell omics technologies only provide one type of molecular information (DNA, mRNA, proteins, metabolites). These measurements provide incomplete information because the cell phenotype is determined by multiple layers of biomolecules and the interplay between genome, epigenome, transcriptome, proteome, and metabolome. For example, mRNA abundance in one cell cannot be precisely referred to the corresponding DNA and proteins in other cells because of the potential subtle difference in genotype (e.g. somatic mutation or copy number variation in cancer) or phenotype (e.g. tumor immune microenvironment and epithelial-mesenchymal transition).

Analytical technologies typically employ antibodies for targeted protein measurements, which significantly limits the number of proteins being analyzed (<100 targets). Also, antibody-based labeling is typically limited to cell surface proteins. The quantification accuracy is largely determined by the quality of antibodies (specificity and purity) and can be suboptimal.

The present disclosure provides apparatuses and methods that overcome many of these disadvantages.

SUMMARY

Methods for performing multiple omics analysis in parallel are provided. The methods can include: providing a mixture of cellular components acquired from the same cell; dividing the mixture into at least a first portion and a second portion; performing a first analysis on the first portion to acquire a first set of analytical data; performing a second analysis on the second portion to acquire a second set of analytical data, wherein the first and second analyses comprise different analytical techniques and provide different sets of analytical data; and processing the first and second sets of analytical data to determine the omics of the cell.

Methods for forming mixtures of analytes into first and second portions are also provided. The methods can include: providing a first mixture of first analytes within a first solution upon a first plate, the first mixture defining at least one first exposed surface; providing a second solution upon a second plate, the second solution defining at least one second exposed surface; and aligning the first and second plates to engage the first exposed surface with the second exposed surface, wherein the engaging is sufficient to convey at least some of the first analytes into the second solution to form a second mixture of the first analytes.

DRAWINGS

Embodiments of the disclosure are described below with reference to the following accompanying drawings.

FIG. 8 depicts analytical data when using methods according to embodiments of the disclosure.

DESCRIPTION

This disclosure is submitted in furtherance of the constitutional purposes of the U.S. Patent Laws "to promote the progress of science and useful arts" (Article 1, Section 8).

The present disclosure provides at least one route for overcoming the limitations of the prior art using a mass spectrometry-based proteomics approach. With the advance of microfluidic sample preparation and isobaric labeling, single-cell proteomics (i.e., "scProteomics") is capable of measuring thousands of proteins from single cells in unbiased manners. Using methods of the present disclosure, multimodal transcriptome-proteome measurements can be acquired from the same single cell by integrating single-cell RNA sequencing (scRNAseq) with scProteomics. To improve integration, nanoSPLITS technology (i.e., nano-droplet SPlitting for Linked-multimodal Investigations of Trace Samples) was developed as a method capable of equally dividing nanoliter-scale cell lysates via two droplet microarrays and separately measuring them with RNA sequencing and mass spectrometry. In accordance with example methods, NanoSPLITS provides high-efficiency proteomic preparation of single cells by miniaturizing the assay volumes to nanoliter scale volumes. The reaction miniaturization of the present methods reduces non-specific adsorption-related sample losses, but can also enhance enzymatic digestion kinetics. The use of nanoliter droplets can improve overall sample recovery of both mRNA transcripts and proteins for sensitive single-cell multiomics.

Figure 1:
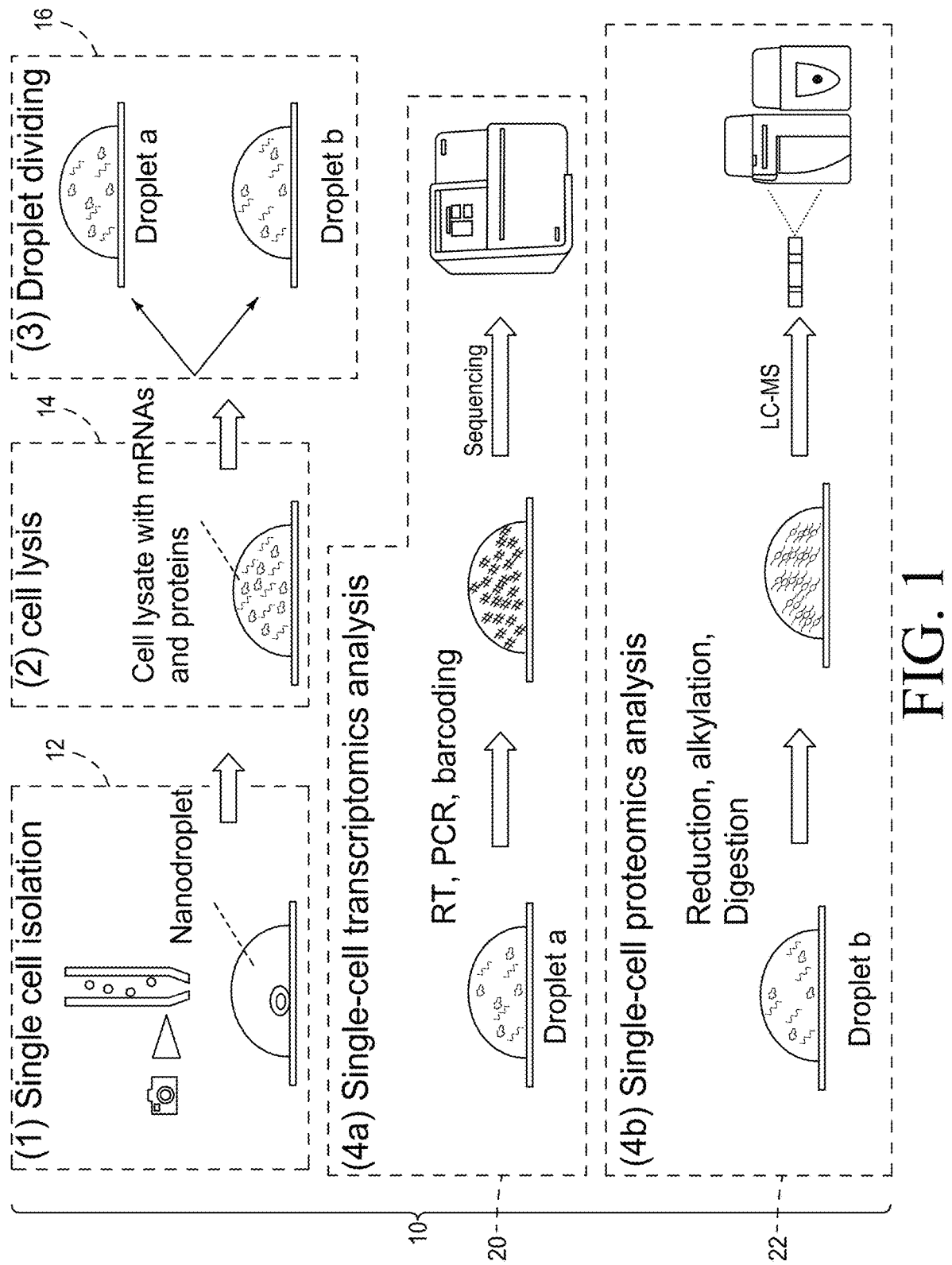
FIG. 1 is an example method flow according to an embodiment of the disclosure.
Figure 1:
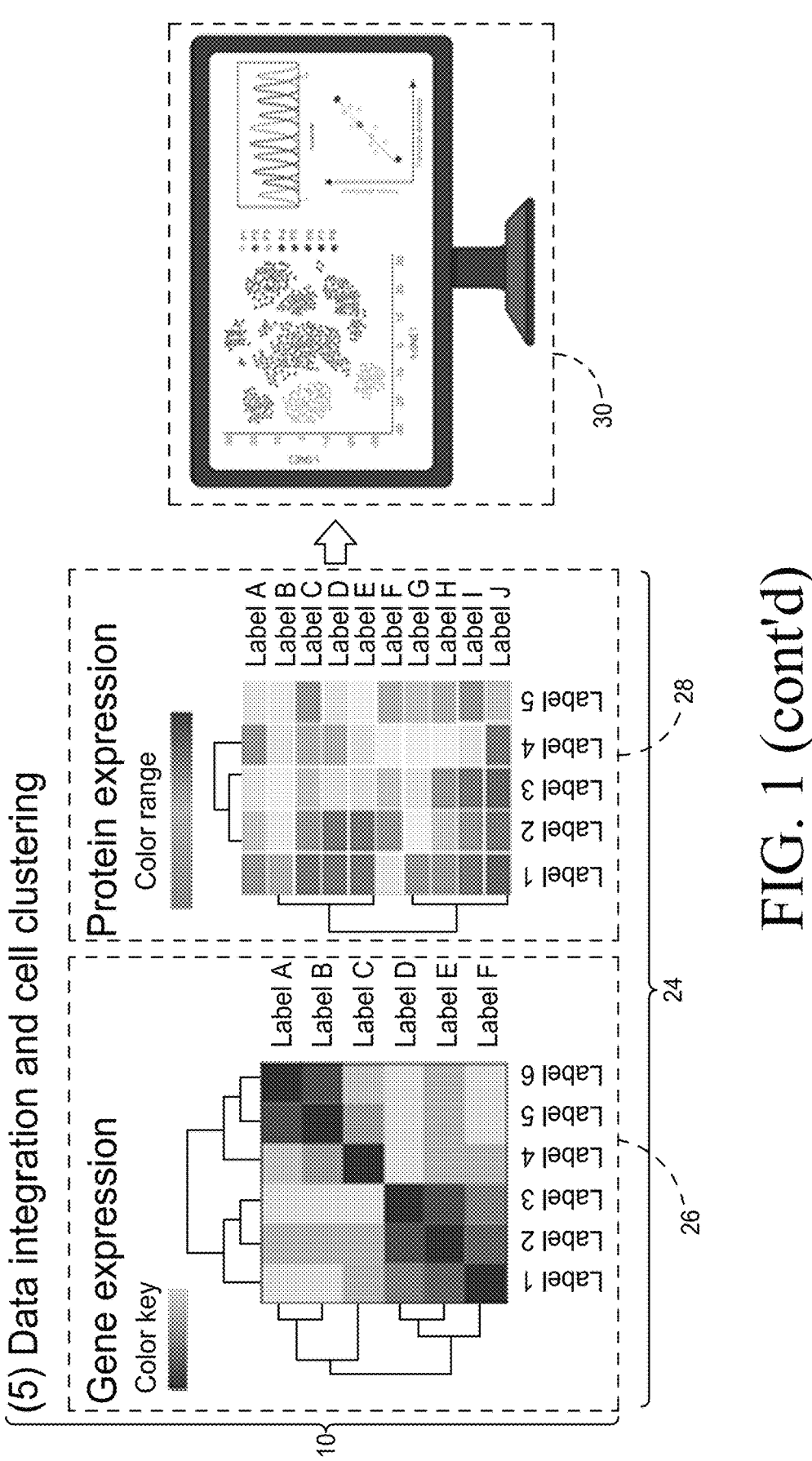

The present disclosure will be described with reference to FIGS. 1-20E. Referring first to FIG. 1, method 10 for performing multiple omics Analysis in parallel is depicted. Method 10 can include providing a mixture of cellular components 12/14. This mixture can be a mixture of a single cell within a solution, multiple cells within a solution, processed components of single cell (same cell) within a solution, and/or processed components of multiple cells within a solution acquired from the same cell. These cells or components can be divided 16 into at least a first portion 20 (e.g., droplet a) and a second portion 22 (e.g. droplet b). A first analysis 20 can be performed on the first portion to acquire a first set of analytical data (e.g., sequencing), and, in parallel, a second analysis 22 can be performed on the second portion to acquire a second set of analytical data (e.g., LC-MS data). The first and second analysis are different analytical techniques and provide different sets of analytical data. Method 10 can then include processing 24 the first 26 and second 28 sets of analytical data to determine the omics 30 (e.g. RNA expression and/or protein expression) of the cell.

In accordance with the present disclosure and with reference to FIG. 1, at (1) single cells are isolated into a nanoliter droplet(s) using a cell sorter; at (2) the cell is lysed (processed) to release mRNA and protein molecules; at (3) the cell lysate is divided into two droplets; at (4a) mRNAs are reversely transcribed, PCR amplificated, and barcoded to generate sequence library (analyzed and analytical data provided); at (4b) proteins are reduced, alkylated, and tryptic digested for LC-MS analysis. At (5), RNA and protein expression data are extracted and integrated for analysis.

In accordance with the above methods, parallel measurement of multiple molecular types in the same single cells can offer unique insights compared with measuring them separately in different single cells. These methods can provide high-throughput single-cell multiomics (scMultiomics) data to assess multiple different types of molecules in the same single cells in parallel. Several analytical techniques can be utilized to determine cell characteristics (e.g., co-measure multiple different types of molecules in single cells). The technologies can include DNA-mRNA, DNA methylation-mRNA, and/or chromatin accessibility-mRNA, for example. To integrate proteomics measurement into scMultiomics, two strategies were used. In the first strategy, DNA-oligonucleotide-conjugated antibodies were used to label cell surface proteins, followed by reverse transcription, PCR amplification, and sequencing to quantify protein/mRNA abundance simultaneously. In the second strategy, both mRNA transcripts and proteins are labeled by metal isotopes for mass cytometry measurement.

As part or separate from, as will be described with reference to FIGS. 5A-C, droplet merge-and-split technology can be utilized. For example, after a single-cell is lysed in a nanodroplet array, the droplet array is merged with a blank droplet array to allow fast mixing between paired droplets for dividing. Hundreds even thousands of samples can be processed in parallel to achieve high throughput. After separating the two arrays, single-cell lysate will be equally split into two droplet reactors in a pipetting-free fashion. Elimination of pipetting steps reduces the risk of contaminations. The use of nanoliter droplets also provides high sample recovery and high-efficiency sample processing. The plate surfaces can be modified to specifically enrich different types of molecules. For example, the surface can be modified to be hydrophobic to enrich proteins from cell lysates; alternatively, the surface can be modified with poly-T oligos to enrich mRNA molecules. It is possible to reach close to 100% recovery for different types of molecules based on surface chemistry. The mixing of two droplet arrays and the enrichment can be enhanced by multiple rounds of "droplet merge-and-split". For high throughput analysis, after droplet split, barcode approaches can be used for multiplex analysis.

In accordance with the present disclosure, nanoscale sample preparation methods and apparatus are provided that can be used to perform parallel analysis of many different types of molecules in small amounts of biological samples, down to single cells.

In accordance with example implementations, the first or second analysis can include mRNA, DNA, protein, lipid, metabolite, and/or phenotype analysis. Accordingly, the first or second analysis can include sequencing strategies such as DNA, DNA methylation, and/or chromatin accessibility. Also, the first or second analysis can include mass spectrometry analysis.

As described herein, the mixture or cellular components can be provided from at least one cell, or the cellular components can be provided from between 1 and 100 cells. Accordingly, the methods of the present disclosure can include separating a cell mixture to provide the at least one cell and processing at least one cell to form the mixture of cellular components. The processing of the cell(s) can include lysing at the cell or cells.

In accordance with FIG. 1, single cells or a low number of cells are isolated into nanodroplets, followed by cell lysis to release intracellular molecules, such as DNAs, RNA transcripts, proteins, and metabolites. At the same time, an array of blank droplets was loaded on a different chip (plate). Next, the two chips (plates) are aligned together to allow one-to-one droplet merging (FIGS. 5A-5C). The assembled droplet chips can then be incubated to allow efficient mixing between droplet pairs. Finally, the two chips are separated to split the merged droplet and divide molecules in the two chips. As an initial demonstration of the technology, mRNA transcript and proteins were co-measured using RNA sequencing and mass spectrometry methods, respectively.

Next, the surface chemistry of two droplet array chips is adjusted to specifically enrich different types of molecules. The surface can be modified to be hydrophobic to enrich proteins from cell lysates; alternatively, the surface can be modified with poly-T oligos to enrich mRNA molecules. The merge-and-split workflow can be performed for many cycles to enhance mixing and allow efficient enrichment on nanowell surfaces. The method with integrated transcriptomics and proteomics of single cells was demonstrated. It can be applied to other omics analysis, such as mRNAs/metabolites proteins/metabolites; intact proteins/digested proteins, etc.

In addition to the information provided in the following description the following advantages are also present: For multiplexing analysis, after droplet splitting, the RNA transcripts can be barcoded during reverse transcription, then cDNAs from all the cells could be simultaneously pooled for PCR amplification and sequencing. Alternatively, the barcoding process can be performed after reverse transcription using indexed PCR primers. The plate can have nanowell surfaces modified to enrich or repel specific types of molecules. For example, the nanowell can be modified with hydrophobic silanes (C2, C4, or C8) to enrich proteins while repelling mRNA molecules. Alternatively, the surface can be modified with ploy-T oligos or DNA oligos with predefined sequences to enrich mRNA molecules. The split ratios between the nanodroplet array can be adjusted by changing the droplet volumes. The split ratios can be adjusted by tuning the surface properties or using detergents to modify the surface tensions.

Figure 2:
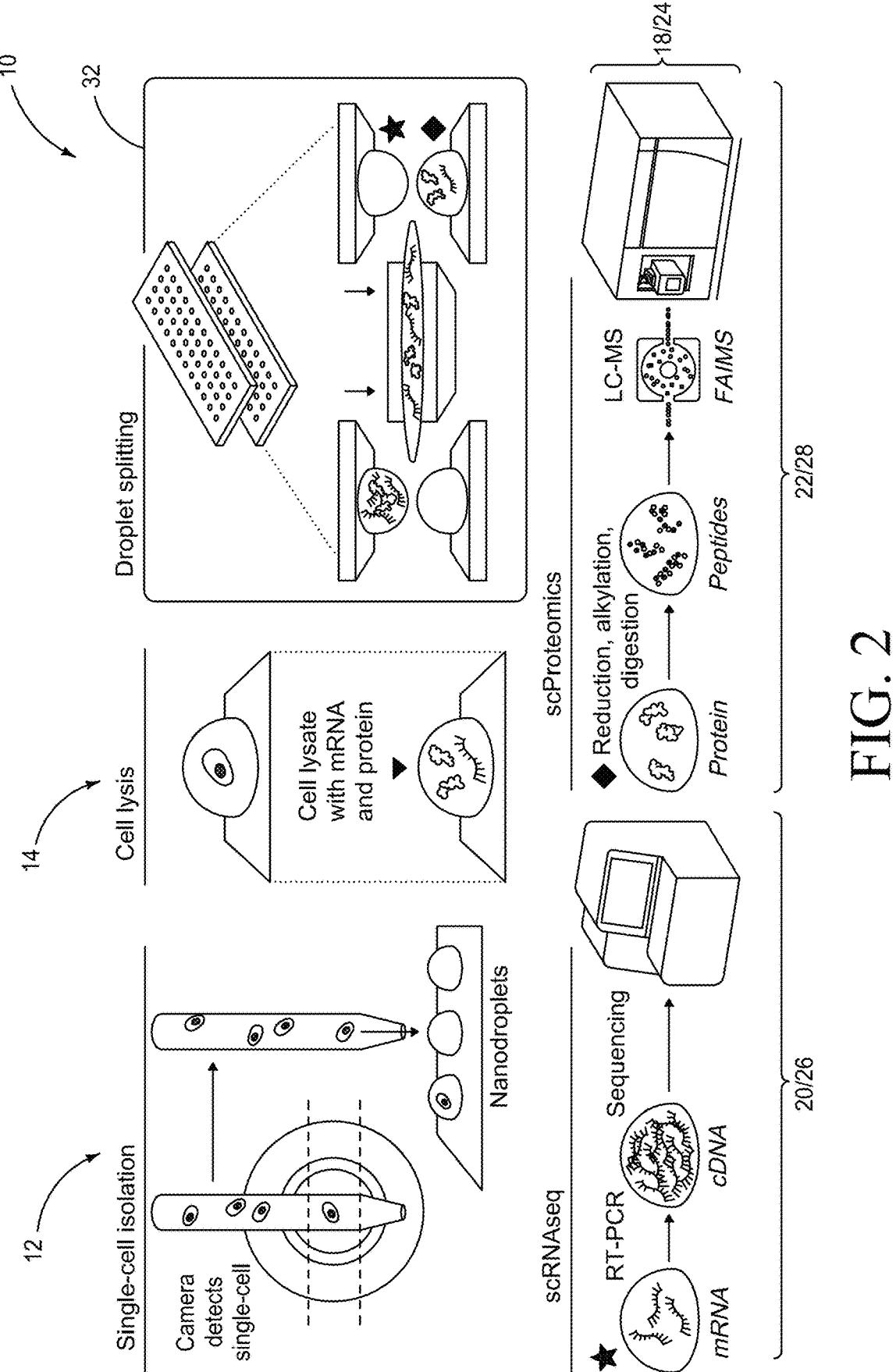
FIG. 2 is an example method flow using the methods of forming mixtures of analytes according to an embodiment of the disclosure.

The overall workflow of the nanoSPLITS-based single-cell multiomics platform is also illustrated in FIG. 2, a schematic illustration showing the workflow including cell sorting, lysis, droplet merging/mixing, and droplet separation for downstream scRNAseq and scProteomics measurement. (As used herein "nanoSPLITS" refers to either or both of methods for performing multiple omics analysis in parallel alone or in combination with methods for forming mixtures of analytes into at least first or second portions, and/or the methods for forming mixtures alone). As shown, an image-based single-cell isolation system is employed to directly sort single cells into an optimized lysis buffer, followed by a freeze-thaw cycle to achieve cell lysis. Next, the microchip containing single-cell lysate is manually aligned with a separate chip containing only cell lysis buffer. The droplet arrays in the two chips were merged and separated for three rounds to achieve complete mixing. One chip containing approximately half of the cell lysate can then be transferred into 384-well plate for scRNAseq based on Smart-seq 2. For scProteomics, the remaining ~50% lysate is digested with a sample preparation protocol with n-Dodecyl-beta-Maltoside (DDM) as surfactant and directly analyzed with an ion-mobility-based MS data acquisition method. Notably, when the same droplet volume (200 nL) was used in an evaluation experiment with a model fluorescent dye, the methods for forming mixtures of the present disclosure can achieve splitting ratios between 46% to 47%, with 50% representing an equal split.

A cell lysis buffer that is compatible with both scProteomics and scRNAseq analyses can be utilized. For example, scProteomics utilizes a buffer containing 0.1% DDM to reduce non-specific binding of proteins to surfaces, while scRNAseq includes recombinant protein-based RNase inhibitors to reduce mRNA degradation. To evaluate their impacts on both methods, these additives were tested in a moderately buffered hypotonic solution (10 mM Tris, pH 8) with 20 mouse alveolar epithelial cells (C10). The inclusion of 1×RNase inhibitor suppressed proteomic identifications while 0.1% DDM had no significant impact on transcriptomic identifications. Furthermore, the removal of RNase inhibitors from RNAseq analysis had minimal effect on transcriptomic identifications. Accordingly, a 10 mM Tris or HEPES solution with 0.1% DDM were chosen as the cell lysis buffer when performing the methods for forming mixtures of the present disclosure.

Figure 3A:
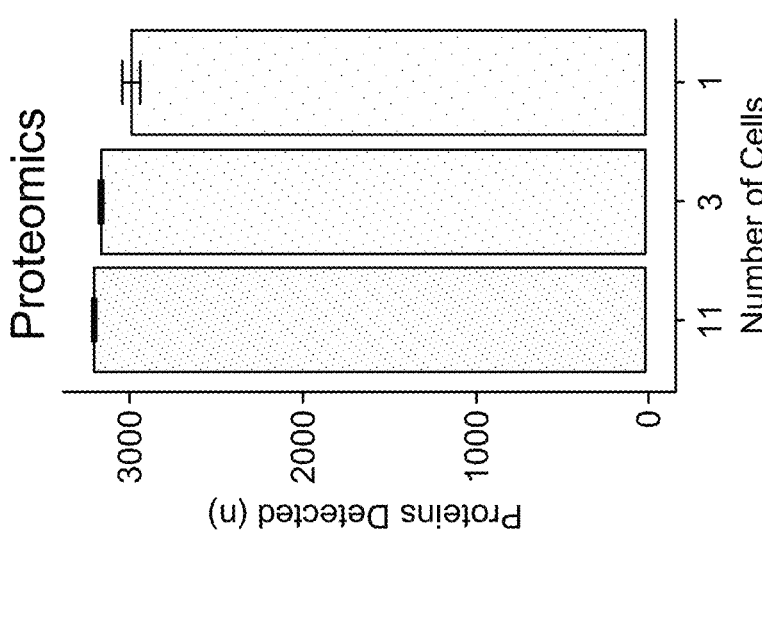
FIGS. 3A-3E depict quantitative and qualitative assessment of transcriptome and proteome measurement methods according to an embodiment of the disclosure.
Figure 3A:
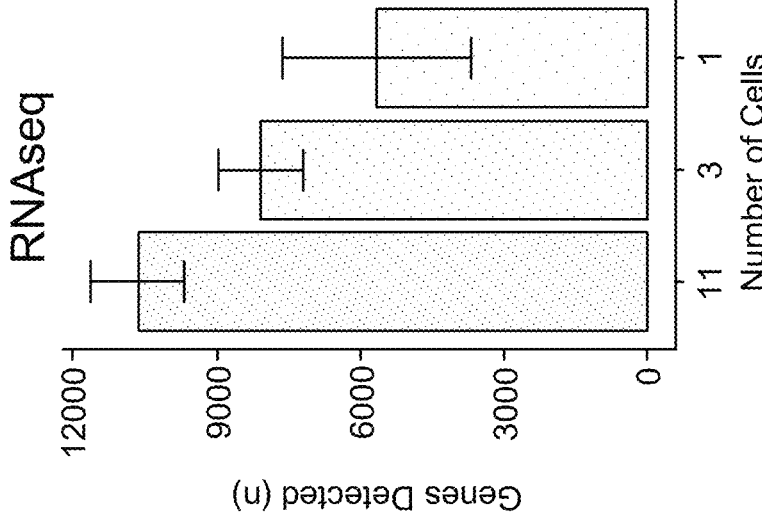
Figure 3B:
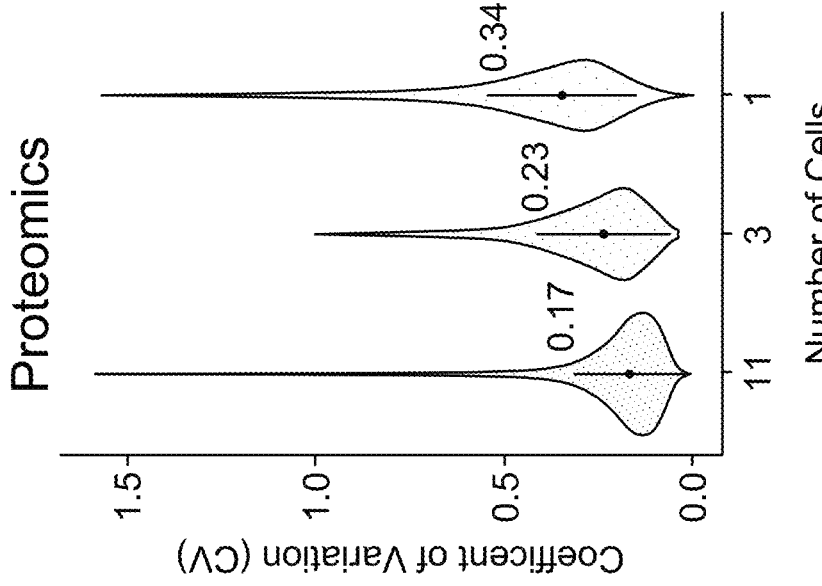
Figure 3B:
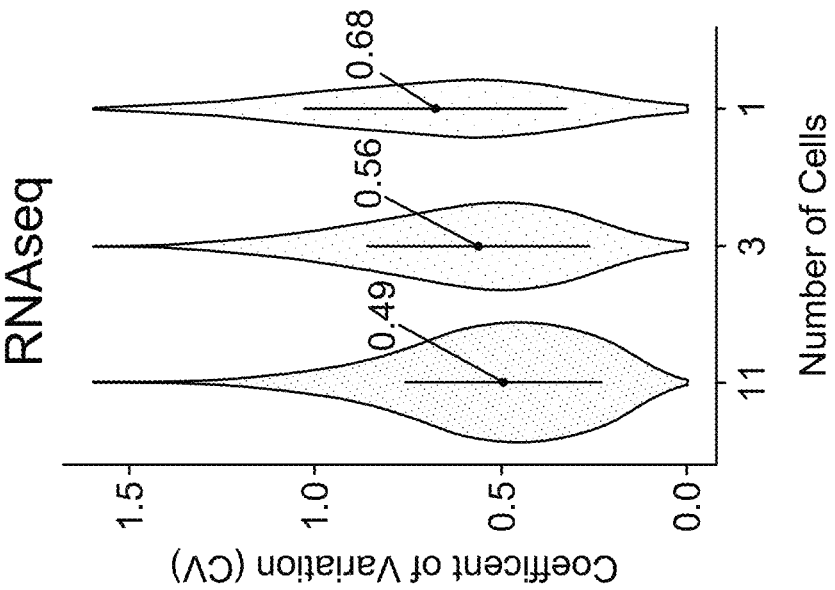
Figure 3C:
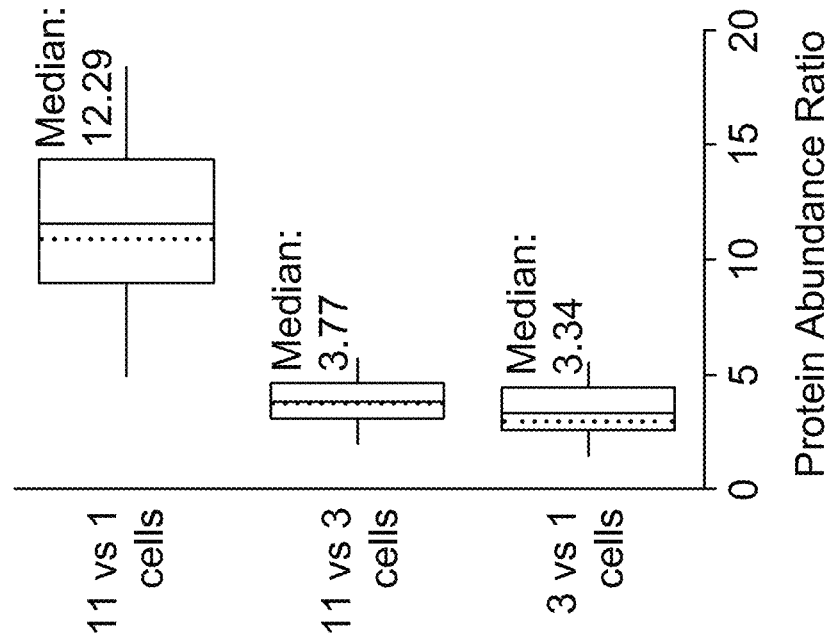
Figure 3D:
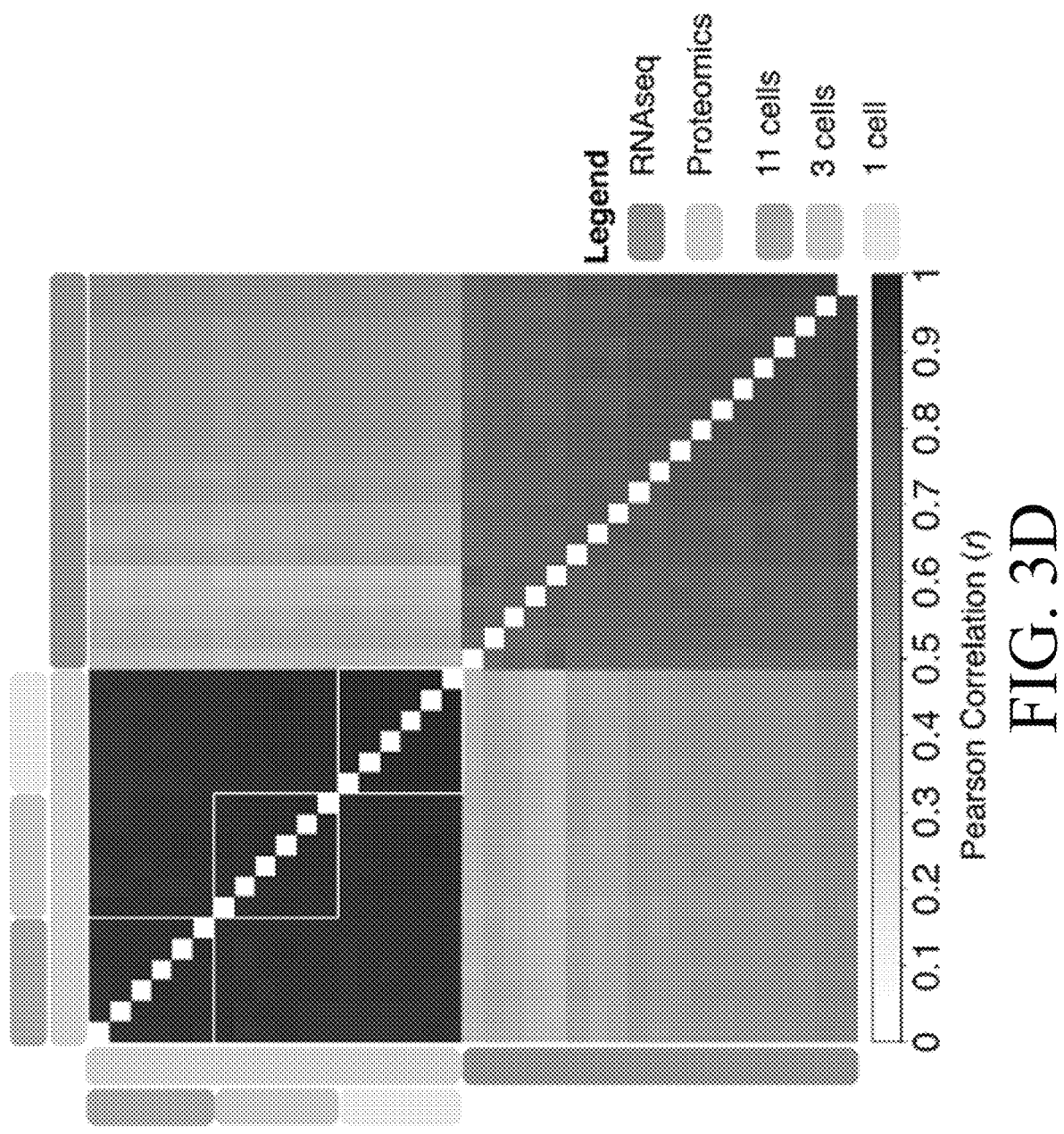
Figure 3E:
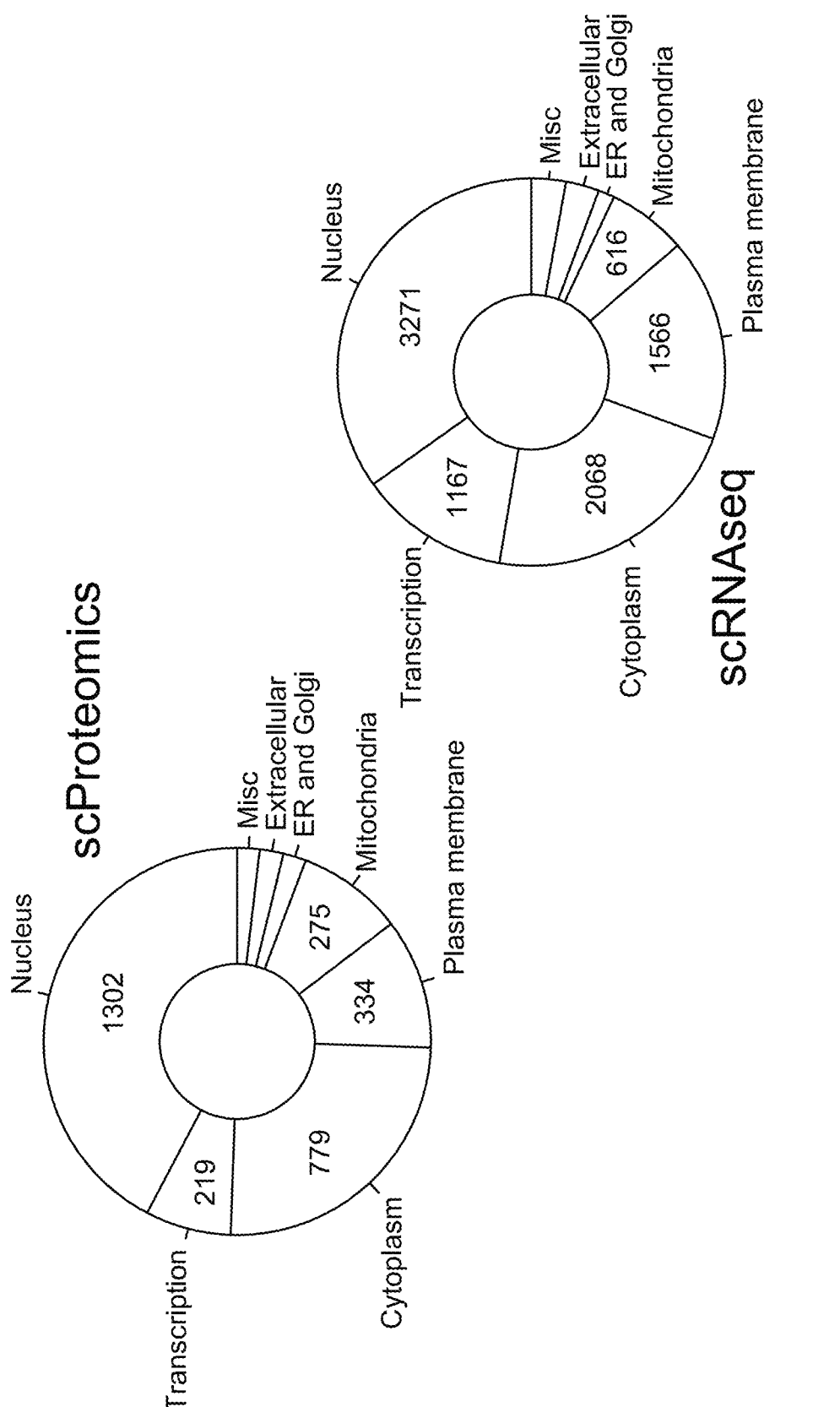

Referring next to FIG. 3A-3E, FIG. 3A shows the average numbers of detected genes and proteins. Error bars indicate standard deviations (+s.d.). FIG. 3B shows distributions of the coefficients of variation (CV) for all proteins and genes with at least 2 observations. Indicated values represent median CV, which is also indicated at the center point within each distribution. FIG. 3C shows the ratios of protein abundance were calculated for comparisons between the different pooled cell samples (11 vs 1, 11 vs 3, and 3 vs 1). Experimental median is indicated at the black crossbar while the theoretical ratio for each comparison is shown at the dotted line within each boxplot. FIG. 3D shows Pearson correlation heatmap with clustering of transcriptomics and proteomics results. In FIG. 3E, cellular component gene ontologies were determined for each gene (scRNAseq) and protein (scProteomics) detected in the single-cell data.

To evaluate the methods of the present disclosure, several quantities (11, 3, and 1) of C10 cells were sorted and measured using the workflow. Considering a 5 read minimum per gene for transcriptome identification and 1% FDR cutoff for protein identification, robust coverage of both genes and proteins could be achieved across all tested conditions (FIG. 3A).

Coverage was reduced with the decreasing cell numbers. Single-cell transcriptome and proteome measurements provided 5,848 and 2,934 identifications on average, respectively. The quantitative reproducibility was evaluated for each modality by calculating the coefficients of variations (CVs) of transcriptome and proteome abundances. Median transcriptome CVs ranged from 0.49 for 11 cells to 0.68 for single cells, while proteome median CVs ranged from 0.17 for 11 cells to 0.34 for single cells (FIG. 3B). Modestly higher CVs for single cells were determined, as the mixed cell populations represent averages of the underlying biological variations. Notably, significantly higher CVs were observed for the transcriptome compared to proteome, in agreement with recent reports. Presumably, these higher CVs reflect the dynamic nature of mRNA relative to their protein counterparts, which have longer half-lives on average. The ratios of the measured protein abundances were compared between the different cell populations. The experimental fold differences between the median intensities for 11, 3, and 1 C10 cell are very close to the expected theoretical values (FIG. 3C). For example, the median protein abundance ratio for 3 cells compared to single cells was 3.34, within 12% of the theoretical 3-fold difference. Taken together, these results provide strong evidence that the methods of the present disclosure can provide sensitive and reproducible measurement of both the transcriptome and proteome of the same single cells.

The Pearson correlation coefficients (r) across and within modalities using conceptually-similar normalized transformations for each modality were determined (e.g., FIG. 3D; TPM, transcripts per million for transcriptomics, and riBAQ, relative intensity-based absolute quantification for proteomics). In line with the CV distributions (FIG. 3B), proteomics data had a better agreement between samples compared with transcriptomics data, once again highlighting the dynamic nature of transcriptome where many genes are often expressed in short transcriptional "bursts". The distribution of gene and protein identifications in single cells across several gene ontologies (GO) was calculated to determine if the methods of the present disclosure introduced a bias toward different cellular components due to the nanodroplet splitting process. The scProteomics and scRNAseq were found to have corresponding identifications within cellular components that encompassed all major organelles (FIG. 3E). Furthermore, 1,521 proteins from the scProteomics analyses have GO localizations to the nucleus, 219 of which of have known roles in transcription. This is notable as nuclear proteins are typically drivers in gene regulation and transcription, and current multimodal technologies have been limited in the ability to directly measure nuclear protein abundances.

Figure 4A:
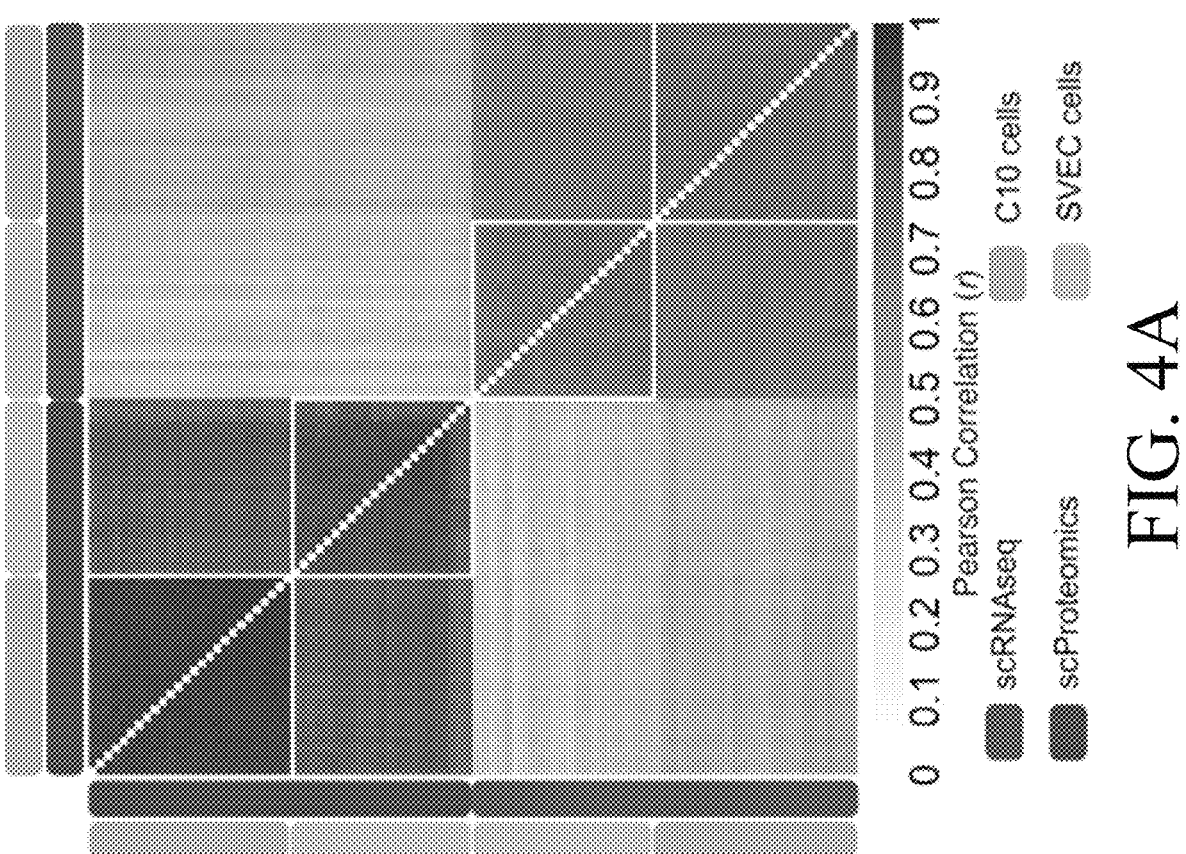
FIGS. 4A-4F depict underlying cell phenotype signatures maintained when using methods according to an embodiment of the disclosure.
Figure 4B:
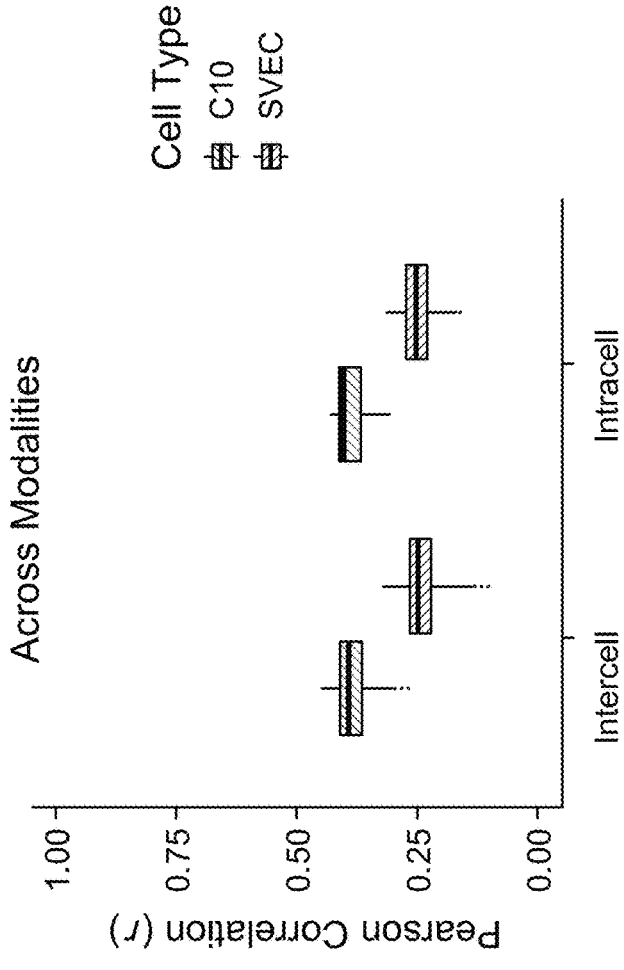
Figure 4B:
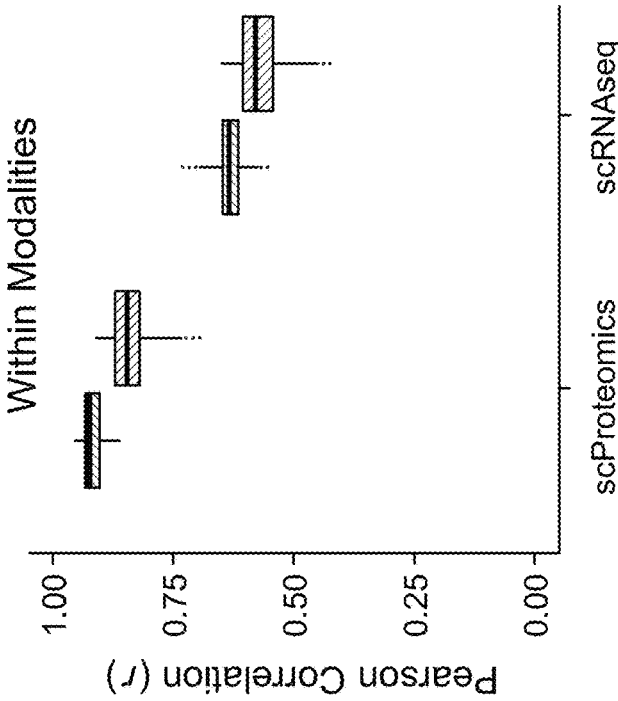
Figure 4C:
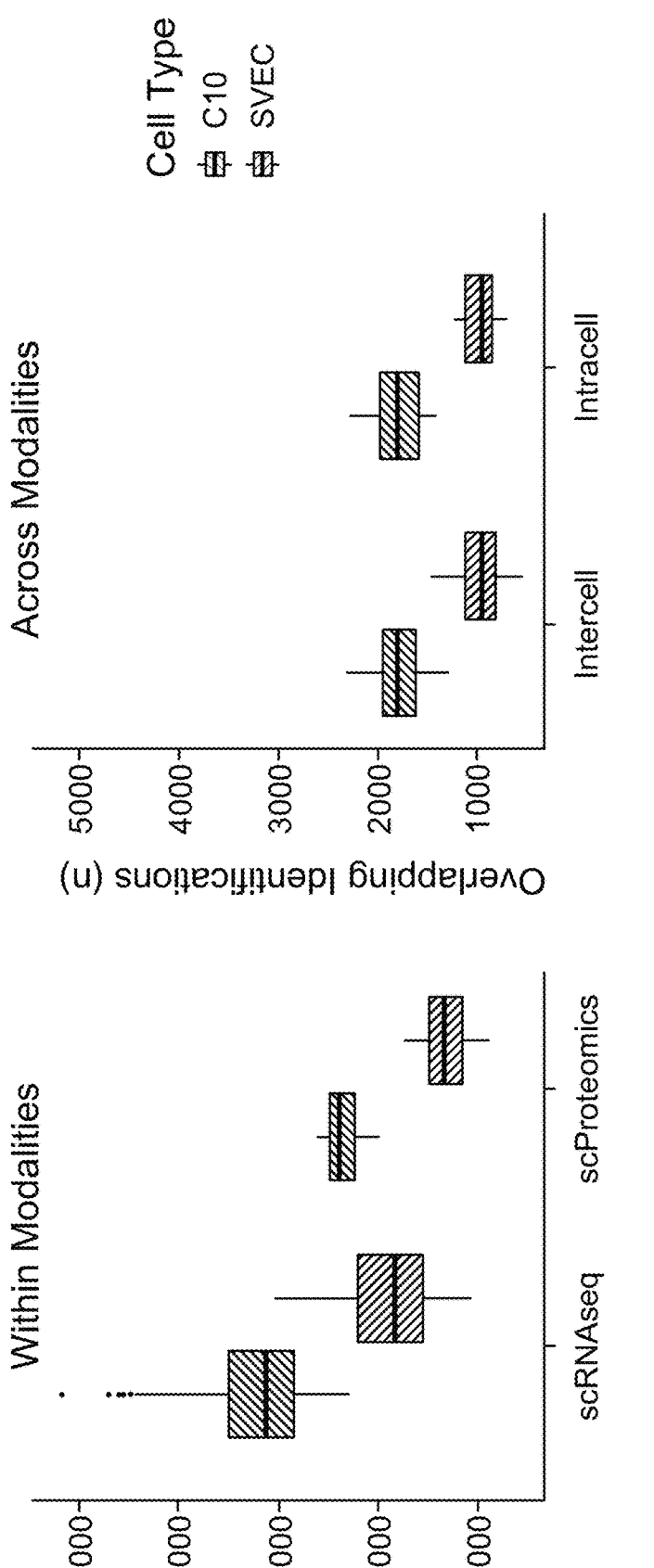
Figure 4D:
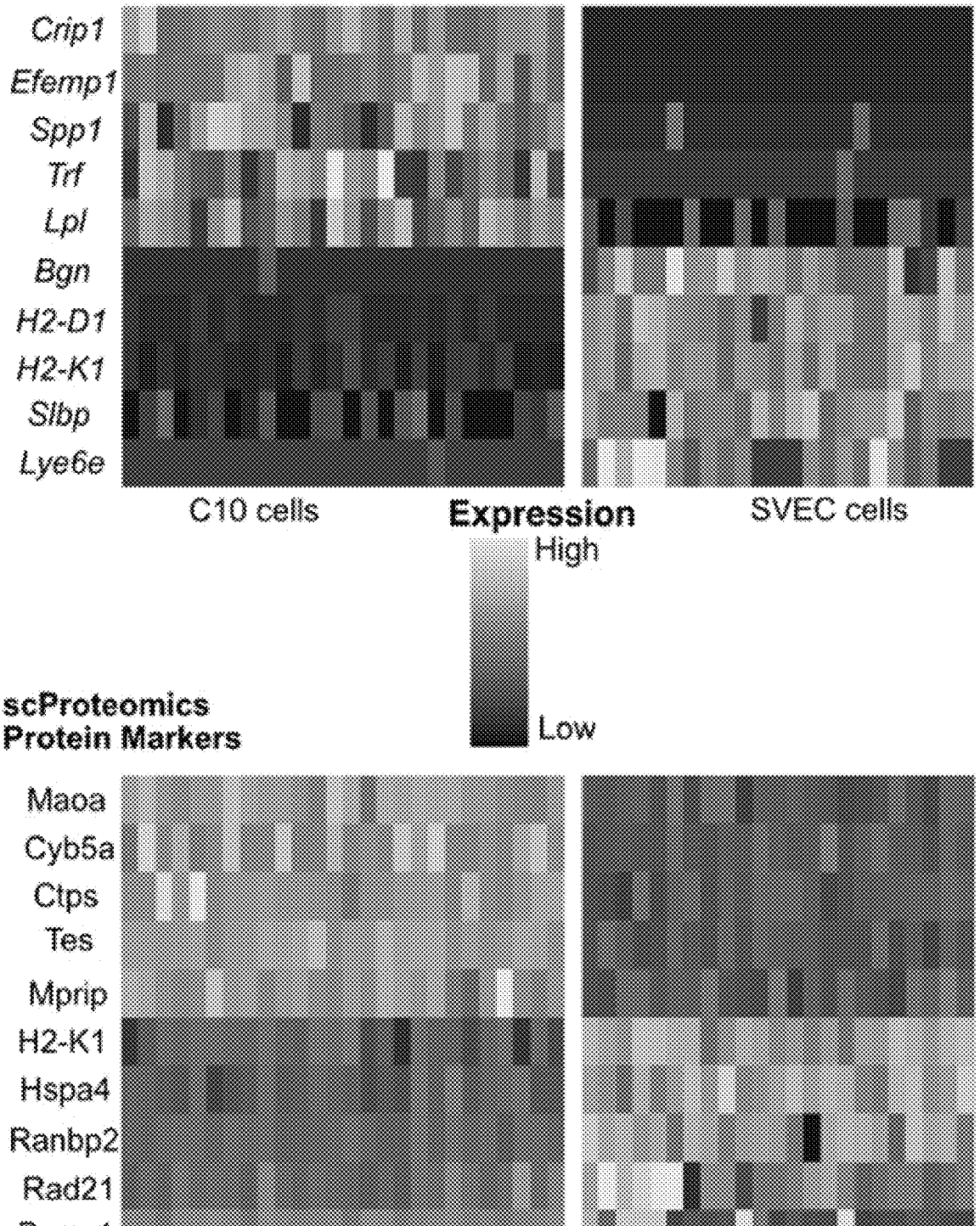
Figure 4E:
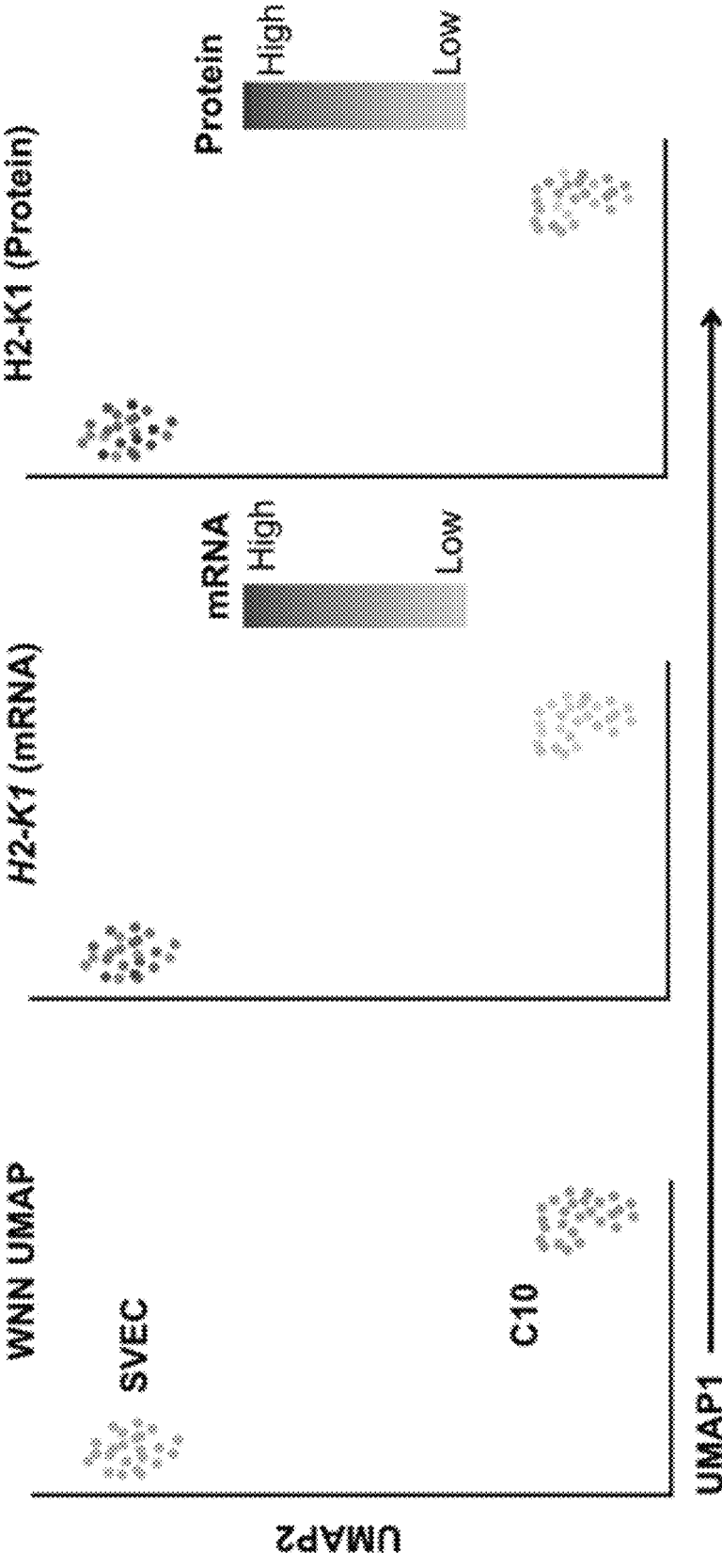
Figure 4F:
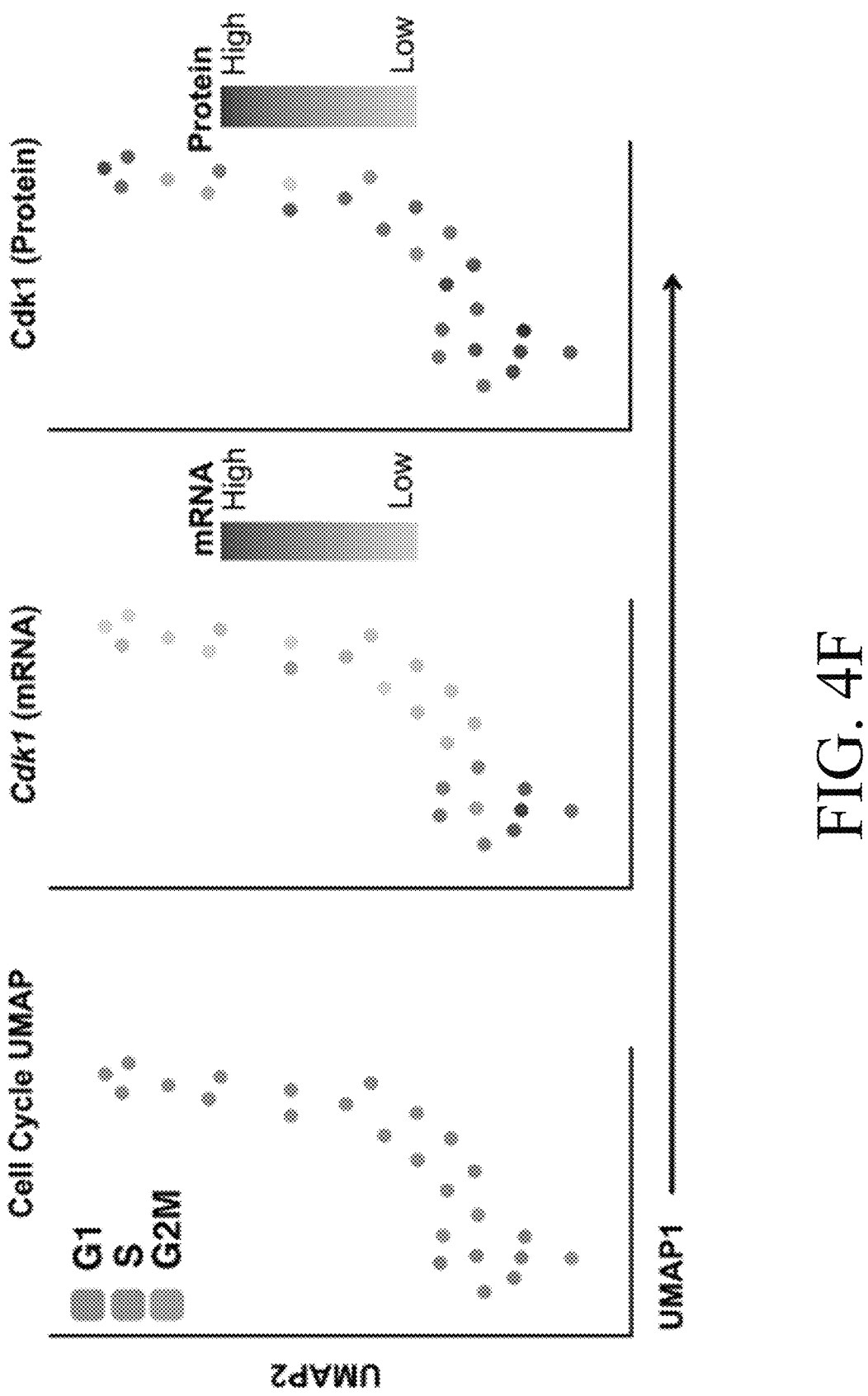

FIG. 4A shows a Pearson correlation heatmap with clustering of transcriptomics and proteomics results for both single C10 and SVEC cells. FIG. 4B shows distributions of Pearson correlations, separated by cell type and modality (scProteomics and scRNAseq). In FIG. 4C, the overlap in gene and protein identifications were determined for each modality separately, as well as across the modalities is shown. In FIG. 4D, top 5 gene markers from scRNAseq data and protein markers from scProteomics data were determined for each cell type. Candidate marker features were determined using a Wilcoxon Rank Sum test (FDR corrected p-values <0.001). FIG. 4E is a weighted-nearest neighbor (WNN) UMAP generated using Seuratto integrate the scRNAseq and scProteomic data. Middle and right panels are based on H2-K1 gene and protein expression, respectively. FIG. 4F is a UMAP generated for C10 cells based on cell-cycle features measured in the scRNAseq data. Middle and right panels are based on Cdk1 gene and protein expression, respectively. All expression values shown in FIGS. 4D, 4E, and 4F are derived from Z-scores after scaling and centering of data.

Having established baseline characteristics of multimodal data, the methods of the present disclosure were then applied to a larger single-cell multimodal analysis encompassing two cell types, mouse epithelial (C10) and endothelial cells (SVEC). In accordance with example implementations, determination of whether the multimodal measurements could precisely distinguish the two cell types and detect gene or protein markers can be sought. As shown in FIG. 4A, both cell types and modalities could easily be clustered based on correlations alone. Within-modality correlations were higher in scProteomics than scRNAseq for both cell types (FIG. 4B). Cross-modality correlation analysis between scRNAseq and scProteomics produced r ranging from 0.31 to as high as 0.56, which fell in the range of previously reported mRNA-protein correlations. Comparison of the cross-modality correlations between the same single cells (intracell) and the correlations between different single cells (intercell) was performed. As shown in FIG. 4B, no significant difference was observed. This is consistent with most of the variation between different cells being attributed to only a small number of genes driving cell cycle progression. These low number of genes would not have a significant impact on global correlations. Overall, SVEC cells had consistently slightly lower correlations, presumably due to their smaller cell size and corresponding reduced measurement depth and precision. The protein/gene overlap analysis demonstrates how measurement depth is strongly linked to cell size (FIG. 4C). On average, C10 cells had ~1,800 overlapping identifications while SVEC cells had ~900 overlapping identifications across modalities.

Next, an evaluation as to whether the multiomics data could be used to identify cell-type-specific marker genes and proteins was performed. FIG. 4D shows the top-5 significant enriched genes and proteins for each cell type. The overlap of these significant markers was relatively low. Despite this, the previously established SVEC-cell marker H2-K1 was identified here at both the protein and mRNA level (FIG. 4D).

Dimensionality reduction with principal component analysis (PCA) showed delineation of both cell types for scRNAseq and scProteomics despite only having half the cell contents. The integration of both modalities through an unsupervised weighted nearest neighbor (WNN) analysis provided robust clustering in the two-dimensional space (FIG. 4E). This also provided the ability to visualize both protein and mRNA abundances, confirming H2-K1 to be a marker that is differentially expressed at the protein and gene level (FIG. 4C). Using canonical cell cycle markers, identification of sub-populations constituting specific cell cycle phases was performed, demonstrating that even subtle cell to cell variation was retained after the droplet splitting process (FIG. 4D). For example, the well-established marker cyclin-dependent kinase 1 (Cdk1) is upregulated at the transcriptional and translational level in S and G2M phase C10 cells.

Taken together, the methods of the present disclosure can provide multimodal profiling of thousands of mRNA transcripts and proteins from the same single cells. The multiomics data allowed precise quantification of the abundances of both mRNA transcripts and proteins and identification of marker genes and proteins from both modalities. Compared with previous technologies that utilize antibodies to infer protein abundances, the methods of the present disclosure can employ mass spectrometry to unbiasedly detect proteins, which is highly valuable for uncovering rare cell populations that lack reliable protein markers. Accordingly, the methods of the present disclosure can be a powerful discovery tool for biomedical applications, such as characterizing tissue heterogeneity and circulating tumor cells. Notably, the present methods are not restricted to the two modalities (transcriptomics and proteomics); other modalities such as lipidomics, metabolomics, genomics, and epigenomics can conceptually be integrated into the workflow. As more analytical frameworks for integrating multimodal data are created, it is believed the methods of the present disclosure can provide greater insight into how different modalities interact with each other to control single-cell phenotypes in various contexts such as perturbations, mitosis/meiosis, and differentiation.

Although a low throughput approach was employed in some of these studies, high-throughput multiplexing approaches such as CEL-Seq for transcriptomics and SCOPE-MS for proteomics can be part of the methods of the present disclosure. The integration of multiplexing approaches with the methods of the present disclosure can provide analysis of thousands of single cells with reasonable instrument time and overall cost. Additionally, harmonization across modalities by using multiomic datasets as molecular bridges can be achieved. The generation of proteome and transcriptome bridge datasets can be achieved using the methods of the present disclosure, opening the proteome to reference mapping.

Below are provided more detail regarding the methods and materials used to acquire the date of the previous Figures.

Reagents and chemicals. Deionized water (18.2 MΩ) was purified using a Barnstead Nanopure Infinity system (Los Angeles, CA, USA). n-dodecyl-β-D-maltoside (DDM), iodoacetamide (IAA), ammonium bicarbonate (ABC), and formic acid (FA) were obtained from Sigma (St. Louis, MO, USA). Nuclease-free water (not DEPC-treated), Trypsin (Promega, Madison, WI, USA) and Lys-C (Wako, Japan) were dissolved in 50 mM ABC before usage. Dithiothreitol (DTT, No-Weigh format), acetonitrile (ACN) with 0.1% FA, and water with 0.1% FA (MS grade) were purchased from Thermo Fisher Scientific (Waltham, MA, USA). SMART-Seq V4 Plus kit (Cat #R400753) was purchased from Takara Bio USA.

Design, fabrication, and assembly of the apparatus for forming mixtures of analytes into first and second portions. The apparatus (e.g., FIG. 2: 32, or FIGS. 5A-C: 32a-c) can be fabricated as chips using standard photolithography, wet etching, and silanization as described previously. In accordance with an example implementation, two different chips can be provided. Both contained 48 (4×12) nanowells with a well diameter of 1.2 mm. The inter-well distance for the first chip was 2.5 mm while the second was 4.5 mm. Chip fabrication utilized a 25 mm×75 mm glass slide pre-coated with chromium and photoresist (Telic Company, Valencia, USA). After photoresist exposure, development, and chromium etching (Transene), select areas of the chip were protected using Kapton tape before etching to a depth of ~5 μm with buffered hydrofluoric acid. The freshly etched slide was dried by heating it at 120° C. for 1 h and then treated with oxygen plasma for 3 min (AP-300, Nordson March, Concord, USA). 2% (v/v) heptadecafluoro-1,1,2,2-tetrahydrodecyl-dimethylchlorosilane (PFDS, Gelest, Germany) in 2,2,4-trimethylpentane was applied onto the chip surface and incubated for 30 min to allow for silanization. The remaining chromium covering the wells was removed with etchant, leaving elevated hydrophilic nanowells surrounded by a hydrophobic background. To prevent retention of mRNA via interaction with free silanols on the hydrophilic surface of the nanowells, freshly etched chips were exposed to chlorotrimethylsilane under vacuum overnight to passivate the glass surface. A glass frame was epoxied to a standard glass cover slide so that it could be easily removed from the 2.5 mm inter-well distance chips for droplet splitting. For the 4.5 mm inter-well distance chips, PEEK chip covers were machined to fit the chip. Chips were wrapped in parafilm and aluminum foil for long-term storage and intermediate steps during sample preparation.

Cell culture. Two murine cell lines (NAL1A clone C1C10 is referred to as C10 and is a non-transformed alveolar type II epithelial cell line derived from normal BALB/c mouse lungs; SVEC4-10, an endothelial cell line derived from axillary lymph node vessels) were cultured at 37° C. and 5% $CO_2$ in Dulbecco's Modified Eagle's Medium supplemented with 10% fetal bovine serum and 1× penicillin-streptomycin (Sigma, St. Louis, MO, USA). The cultured cell lines were collected in a 15 ml tube and centrifuged at 1,000×g for 3 min to remove the medium. Cell pellets were washed three times by PBS, then counted to obtain cell concentration. PBS was then added to achieve a concentration of $200×10^6$ cells/mL. Immediately before cell sorting, the cell-containing PBS solution was passed through a 40 μm cell strainer (Falcon™ Round-Bottom Polystyrene Test Tubes with Cell Strainer Snap Cap, FisherScientific) to remove aggregated cells.

Cell sorting. Before cell sorting, chips (e.g., FIGS. 5A-5C: 62 and 52) were prepared by the addition of 200-nL hypotonic solution consisting of 0.1% DDM in 10 mM Tris to each nanowell. A CellenONE instrument equipped with a glass piezo capillary (P-20-CM) for dispensing and aspiration was utilized for single-cell isolation. Sorting parameters included a pulse length of 50 μs, a nozzle voltage of 80 V, a frequency of 500 Hz, a LED delay of 200 μs, and a LED pulse of 3 μs. The slide stage was operated at dew-point control mode to reduce droplet evaporation. Cells were isolated based on their size, circularity, and elongation in order to exclude apoptotic cells, doublets, or cell debris. For C10 cells, this corresponded to 25 to 40 μm in diameter, maximum circularity of 1.15, and maximum elongation of 2, while SVEC cells were 24 to 32 μm in diameter, maximum circularity of 1.15, and maximum elongation of 2. All cells were sorted based on brightfield images in real time. The pooled C10 experiment had 11, 3, and 1 C10 cells sorted into each nanowell on a single 2.5 mm inter-well distance chip. For the SVEC and C10 comparison experiment, a single 48 well chip with 4.5 mm inter-well distance was used for each cell type and had a single cell sorted into each well. To perform the transferring identifications based on FAIMS filtering (TIFF) methodology for scProteomics, a library chip was also prepared containing 20 cells per nanowell, with each cell type sorted separately on the same chip to reduce technical variation. After sorting, all chips were wrapped in parafilm and aluminum foil before being snap-frozen and stored at −80° C., which partially served to induce cell lysis via freeze-thaw.

Cell Omics with Mixing in parallel. To accomplish splitting of the cell lysate, chips were first allowed to thaw briefly on ice. For each split, a complementary chip was prepared that contained the same 200 nL of 0.1% DDM in 10 mM Tris on each nanowell. The bottom chip containing the cell lysate was placed on an aluminum chip holder that was pre-cooled to 4° C. within a PCR workstation (AirClean Systems AC600). Precut ½₂" thick polyurethane foam was placed around wells on the exterior of this bottom chip while the top chip was slowly lowered onto the polyurethane foam. Wells were manually aligned for each chip before manual pressure was applied equally across the chip to merge the droplets for each chip. Pressure was held for 15 seconds before releasing. The droplets were merged twice more following this process. For consistency, the top chip which received 50% of the lysate was used for scRNAseq in all experiments while the bottom chip that initially contained the cell lysate was utilized in scProteomics. After merging, the top chip was immediately transferred into a 96-well or 384-well UV-treated plate containing RT-PCR reagents. For the pooled C10 (11, 3, and 1 cell) experiment, the transfer was performed by adding 1 μL of RT-PCR buffer to each nanowell before withdrawing the entire volume and adding it to a 96-well plate. For the C10 and SVEC comparison experiment, the transfer was accomplished by laying the 4.5 mm inter-well distance chip onto a 384-well plate containing wells with the RT-PCR mix, sealed with a PCR plate seal, and then centrifuged at 3,500×g for 1 minute.

Sample preparation and LC-MS/MS analysis for scProteomics. All post-split chips were first allowed to dry out before sample processing. Protein extraction was accomplished by dispensing 150 nL of extraction buffer containing 50 mM ABC, 0.1% DDM, 0.3× diluted PBS, and 2 mM DTT, and incubating the chip at 60° C. for 60 min. Denatured and reduced proteins were alkylated through the addition of 50 nL 15 mM IAA before incubation for 30 min in darkness at room temperature. Alkylated proteins were then digested by adding 50 nL 50 mM ABC with 0.1 ng/nL of Lys-C and 0.4 ng/nL of trypsin and incubating at 37° C. overnight. The digestion reaction was then quenched by adding 50 nL of 5% formic acid before drying the chip under vacuum at room temperature. All chips were stored in a −20° C. until LC-MS analysis.

An autosampler was employed for LC-MS analysis. The autosampler contains a custom packed SPE column (100 μm i.d., 4 cm, 5 μm particle size, 300 Å pore size C18 material, Phenomenex) and analytical LC column (50 μm i.d., 25 cm long, 1.7 μm particle size, 190 Å pore size C18 material, Waters) with a self-pack picofrit (cat. no. PF360-50-10-N-5, New Objective, Littleton, MA). The analytical column was heated to 50° C. using AgileSleeve column heater (Analytical Sales and services, Inc., Flanders, NJ). Briefly, samples were dissolved with Buffer A (0.1% formic acid in water) on the chip, then trapped on the SPE column for 5 min. After washing the peptides, samples were eluted at 100 nL/min and separated using a 60 min gradient from 8% to 35% Buffer B (0.1% formic acid in acetonitrile).

An Orbitrap Eclipse Tribrid MS (Thermo Scientific) with FAIMSpro, operated in data-dependent acquisition mode, was used for all analyses. Source settings included a spray voltage of 2,400 V, ion transfer tube temperature of 200° C., and carrier gas flow of 4.6 L/min. For the TIFF test samples, ionized peptides were fractionated by the FAIMS interface using internal CV stepping (−45, −60, and −75 V) with a total cycle time of 0.8 s per CV. Fractionated ions within a mass range 350-1600 m/z were acquired at 120,000 resolution with a max injection time of 500 ms, AGC target of 1E6, RF lens of 30%. Tandem mass spectra were collected from the ion trap with an AGC target of 2E4, a "rapid" ion trap scan rate, an isolation window of 1.4 m/z, a maximum injection time of 120 ms, and a HCD collision energy of 30%. For the TIFF library samples, a single CV was used for each LC-MS run with slight modifications to the above method where cycle time was increased to 2 s and maximum injection time was set to 118 ms. Precursor ions with a minimum intensity of 1E4 were selected for fragmentation by 30% HCD and scanned in an ion trap with an AGC of 2E4 and an IT of 150 ms.

RT-PCR, sequencing, and read mapping for scRNAseq. Following the transfer of samples into a 384-well plate containing RT-PCR buffer with 3' SMART-Seq CDS Primer IIA (SMART-Seq® v4 PLUS Kit, TaKaRa, cat #R400753); the samples were immediately denatured at 72° C. for 3 min and chilled on ice for at least 2 min. Full length cDNA was generated by adding RT mix to each tube and incubating at 42° C. for 90 min; followed by heat inactivation at 70° C. for 10 min. 18 cycles of cDNA amplification were done to generate enough cDNA for template library according to SMART-Seq® v4 PLUS Kit instruction. The SMART-Seq Library Prep Kit and Unique Dual Index Kit (TaKaRa, cat #R400745) were used to generate barcoded template library for sequencing. Single-read sequencing of the cDNA libraries with a read length of 150 was performed on NextSeq 550 Sequencing System using NextSeq 500/550 High Output v2 kit (150 cycles, Illumina, cat #20024907). Data quality was assessed with fastqc and read-trimming was conducted using bbduk. Reads were aligned to the mouse genome (Genome Reference Consortium Mouse Build 39) using STAR. BAM file outputs were mapped to genes using htseq-count with default settings. TPM counts were derived using an R script based on TPM procedure.

Database searching and data analysis. All proteomic data raw files were processed by FragPipe version 17.1 and searched against the *Mus musculus* UniProt protein sequence database with decoy sequences (Proteome ID: UP000000589 containing 17,201 forward entries, accessed Dec. 2, 2021). Search settings included a precursor mass tolerance of +/−20 ppm, fragment mass tolerance of +/−0.5 Da, deisotoping, strict trypsin as the enzyme, carbamidomethylation as a fixed modification, and several variable modifications, including oxidation of methionine, and N-terminal acetylation. Protein and peptide identifications were filtered to a false discovery rate of less than 0.01 within FragPipe. For the TIFF method, IonQuant match-between-runs (MBR) and MaxLFQ were set to "TRUE" and library MS datasets were assigned as such during the data import step. An MBR FDR of 0.05 at ion level was used to reduce false matching. FragPipe result files were then imported into RStudio (Build 461) for downstream analysis in the R environment (version 4.1.3).

Figure 5A:
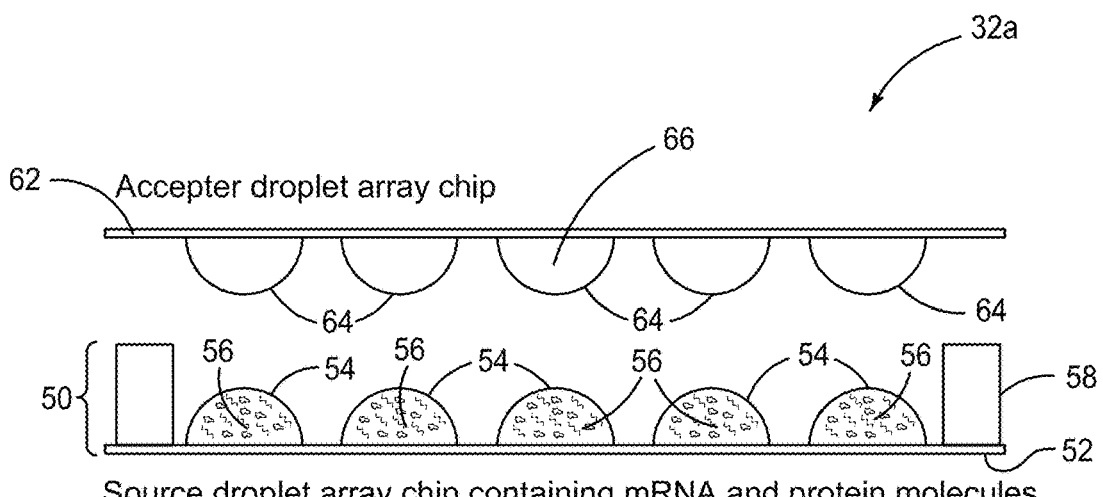
FIGS. 5A-5C depict pipetting-free and parallel dividing single-cell lysate using methods and apparatuses according to an embodiment of the disclosure.
Figure 5B:
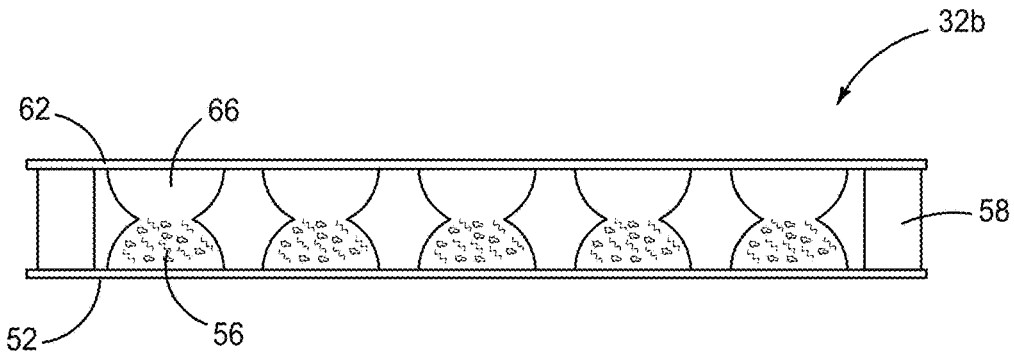
Figure 5C:
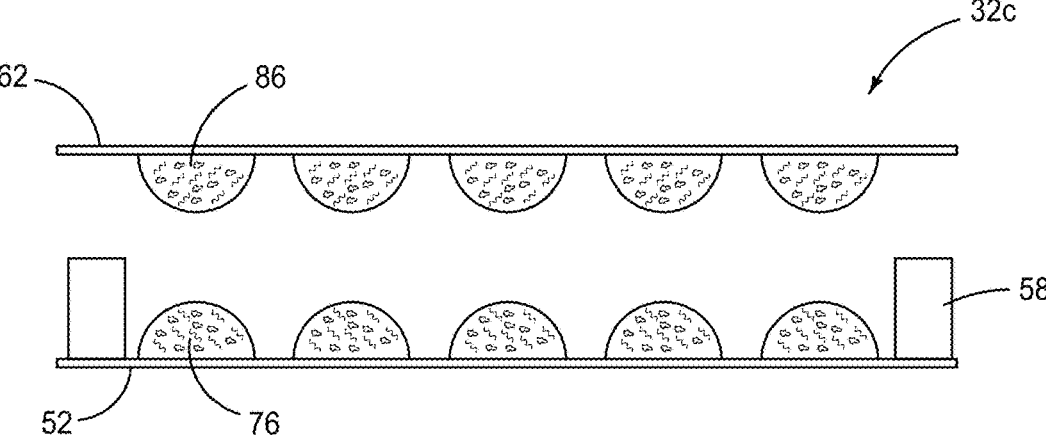
Figures 6A, 6B, 6C:
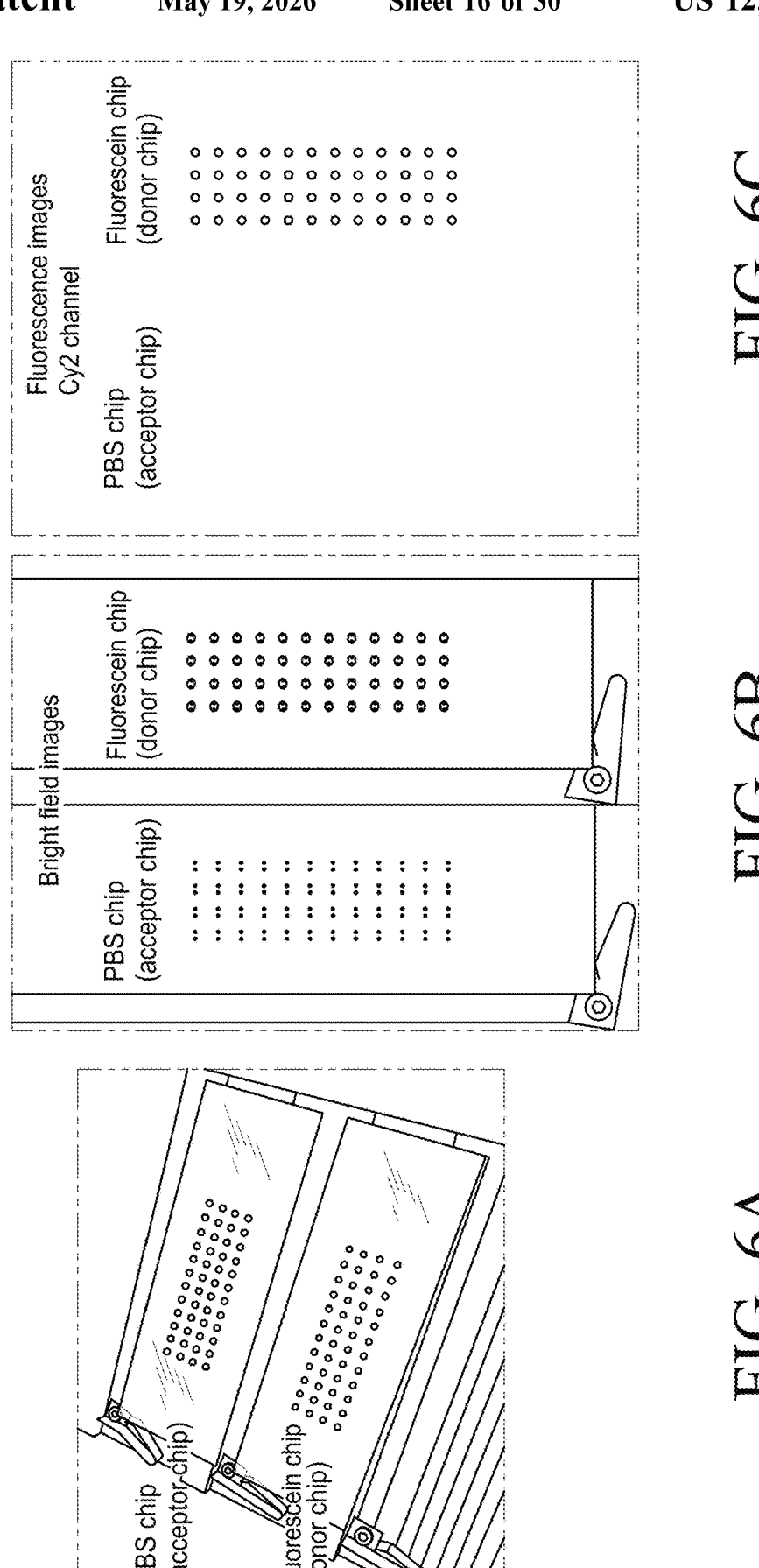
FIGS. 6A-6C depict pre-splitting of chips according to embodiments of the disclosure.
Figures 7A, 7B, 7C:
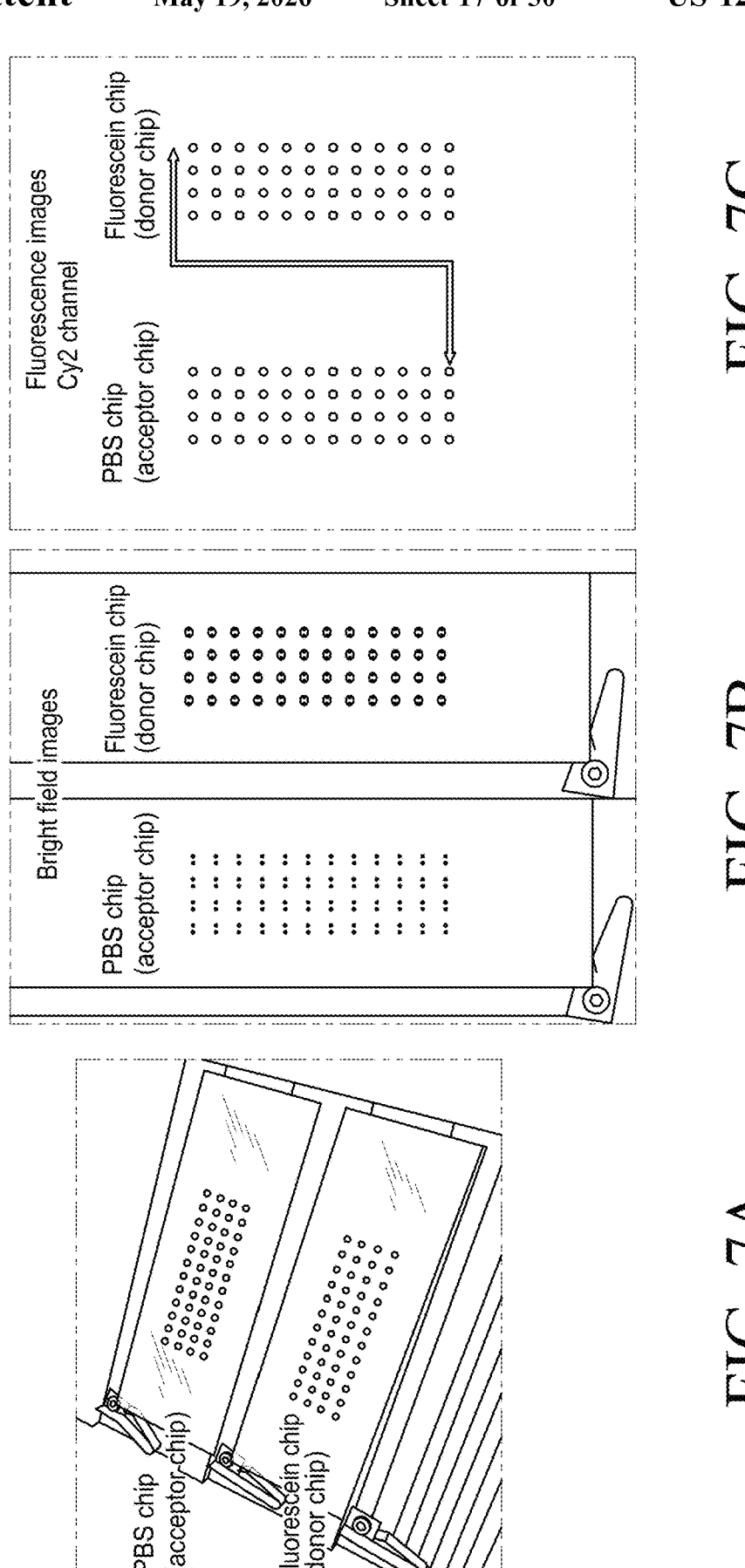
FIGS. 7A-7C depict post-splitting of chips according to embodiments of the disclosure.

Referring next to FIGS. 5A-C, an example method for forming mixtures of analytes into first portion 76 and second portion 86 is depicted. The example method can include plate and mixture configurations 32a-32c. In configuration 32a, a first mixture 56 of first analytes within a first solution upon a first plate 52 is provided. These mixtures can be provided in the form of droplets as shown and having at least one first exposed surface 54. The combination of the components of the solution of the mixture and/or the hydrophobicity of plate 52 can provide for more or less exposed surface. A second solution 66 upon a second plate 62 can be provided. Solution 66 can have at least one second exposed surface 64. Similar to plate 52 and mixture 56, plate 62 and solution 66, the components of the solution and/or the hydrophobicity of the place can provide for more or less exposed surface. The first and second plates can be aligned as shown in 32a, then engaged as shown in 32b to merge the first exposed surface 54 with the second exposed surface 64. The engaging is sufficient to convey at least some of the first analytes into the second solution to form a second mixture 86 of the first analytes as shown in 32c. When separated as shown in FIG. 5C, two separate mixtures 76 and 86 are formed from the mixture 56. To meter the engagement of the plates, spacer 58 can be utilized that dictates the minimum distance between plates 62 and 52. Accordingly, with respect to FIG. 5A, two droplet array chips will be generated: one containing single cell lysate and the other containing blank droplets; in 5B, the two droplet array chips will be aligned and merged; and in 5C, the two chips will be separated to split two droplet array chips, each containing roughly half of cell lysate.

In accordance with example implementations the mixtures can be provided in sets. For example, a first set of first mixtures, and a second set of second solutions can be provided, and the engaging is sufficient to form a second set of second mixtures. As an example, the first set can define a first array and the second set defines a second array. In specific implementations, the number of first mixtures within the first set can be equal to the number of second solutions in the second set. The methods can include disengaging the alignment of the first and second plates to form separated first and second mixtures.

As shown and utilized, each of the first mixture, the second solutions, and the second mixtures can be defined droplets. These droplets can be convex having an outline or surface curved like the exterior of a circle or sphere. The exterior of the convex droplet can protrude away from the plate upon which the droplet is provided thereby forming a surface to engage other droplets. The droplets can have a volume <5 µL. Also, the volumes of first mixture and second solutions can be adjusted to change the split ratio of first analytes. To facilitate the formation of the convex droplet, the first and/or second plates can be provided with a hydrophobic surface, such as an oligo-modified surface.

The methods can also include merging the first or second mixtures with additional solutions to form additional mixtures.

With respect to FIGS. 6A-6C and 7A-7C, to decrease non-specific binding of oligonucleotides to wells, post-split chips were incubated under vacuum for 24 hr with volatilized chlorotrimethylsilane (CTMS). See below for fluorescein methods and materials. These chips containing 48 wells (4×12) were then scrubbed with a cotton ball containing Versa-Clean detergent, rinsed thoroughly with milliQ water, and dried with pressurized $N_2$. A 0.01% 5,6-carboxyfluorescein solution containing 0.1% DDM and PBS solution containing 0.1% DDM were made and placed in the humidity-controlled chamber for dispensing solutions onto the chips. Humidity was set to ~50% and the chillers were set to 16 C. Two chips were placed within the chamber and calibrated. 250 nL of 0.1% DDM in PBS was dispensed onto the 48 wells on one chip, while 250 nL of 0.01% fluorescein, 0.1% DDM was dispensed onto the complimentary chip for splitting. A slide cover was placed on both chips before wrapping them tightly in aluminum foil. The chips were then imaged with AlphaImager FluorChemQ.

Both chips were placed on a chilled aluminum slide-holder and immediately imaged with whitelight field, as well as with fluorescence field with Cy2/3/5 spectral filters. On the donor chip (containing fluorescein) for splitting, two ~2 $cm^2$ of ⅟₃₂″ thick polyethylene foam was placed on the outside edges of the chip. The acceptor chip was slowly lowered onto the bottom-chip, while carefully aligning the wells on both chips. Once the acceptor chip was sitting on the separating foam, equal pressure was applied on the sides of the chip so that the droplets from both chips merged. This pressure was held for 10 seconds before releasing, which separated the droplets. The chips were immediately placed back in the imager and final images were acquired. Quantification of droplet splitting was performed using an open source, image processing program developed by the NIH. This "Fiji" package (version 1.5) can include several plugins that are used routinely in analysis.

With respect to FIG. 8, Cy2 emission spectra images were converted to 16-bit grayscale. A duplicated image was then converted to binary (black/white) to determine droplet area. The droplets outlined by Image J (Fuji package, version 1.5) were then mapped to the original grayscale image for quantification. The mean intensity (relative fluorescence units, RFU) of the acceptor chip droplets was found to be 37.8 +/−1.2 RFU, while the donor chip was 32.8+/−0.7 RFU. This corresponds to a mean droplet splitting efficiency of 47-53%.

Fluorescein methods and materials. For the fluorescein-containing chip (e.g., FIGS. 5A-5C: 62 and 52), 200 nL 0.01% 5,6-carboxyfluorescein solution containing 0.1% DDM was dispensed onto each well. For the PBS-containing chip, 250 nL PBS solution containing 0.1% DDM was dispensed onto each well. A slide cover was placed on both chips before wrapping them tightly in aluminum foil and placing them on ice to prevent evaporation until imaging. For imaging, both chips were placed on a chilled aluminum slide-holder and immediately imaged with whitelight, followed by a Cy2 spectral filter using an AlphaImager FluorChemQ. Following imaging of the unsplit chips, two 2 $cm^2$ of ⅟₃₂″ thick polyethylene foam was placed on one chip. The upper-chip was slowly lowered onto the bottom-chip, while carefully aligning the wells on both chips. Once the upper-chip was sitting on the separating foam, equal pressure was applied on the sides of the chip so that the droplets from both chips merged. Pressure was held for 15 seconds before releasing. The droplets were merged twice more following this process. The post-split chips were immediately placed back in the imager and final images were acquired. Quantification of droplet splitting was performed with the "Fiji" distribution of Image J (Fuji package, version 1.5). Briefly, Cy2 emission images were converted to grayscale. Regions of interest were selected (chip wells) and analyzed using the standard particle analysis in Image J (Fuji package, version 1.5). Each region of interest produced an average pixel intensity that was normalized by droplet area before using for quantification.

Referring to FIG. 8, data is shown when using the methods of the present disclosure to analyze 1, 3, and 10 C10 cells. CellenONE (Cellenion, France) was used to sort mouse C10 cells (PBS) onto chips treated with CTMS coating on the wells. For sample chips (1-4), 200 nL of 0.1% DDM in 10 mM Tris buffer was dispensed first. Cells were then immediately frozen at −80° C., wrapped in aluminum foil until splitting was performed. For splitting, two chips (one containing C10 cells in 200 nL 0.1% DDM in Tris-referred to as "donor", the other with just 200 nL of 0.1% DDM in Tris-referred to as "acceptor") were sandwiched between two pieces of ⅟₃₂″ polyurethane foam placed outside the wells. Droplets were merged for 10 seconds before splitting and performing RNAseq. Proteomic "donor" chip was frozen at −80° C. until MS instrument was ready for use.

Figure 9A:
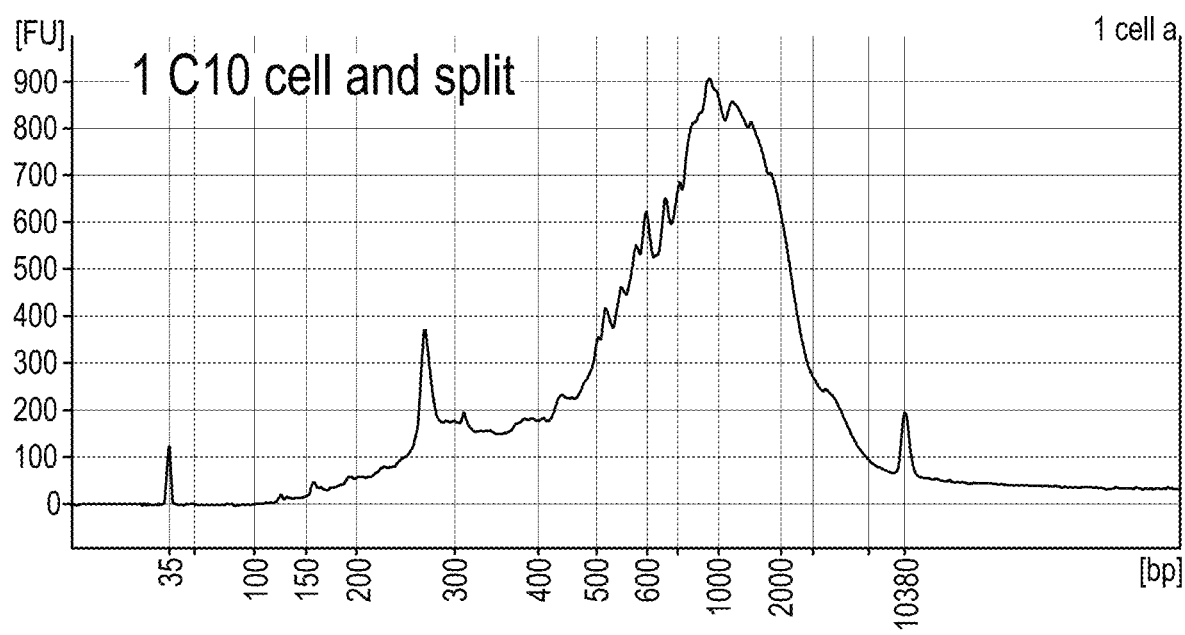
FIGS. 9A-9B depict PCR data to show the RNA presented in accepter droplet.
Figure 9B:
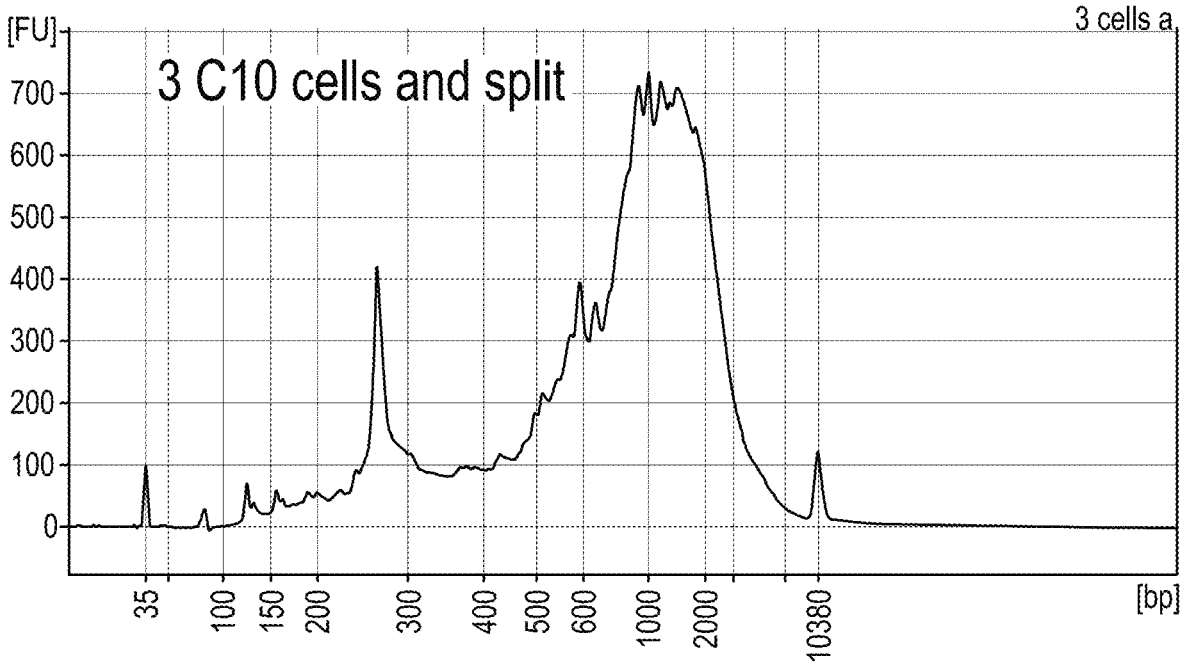
Figure 10B:
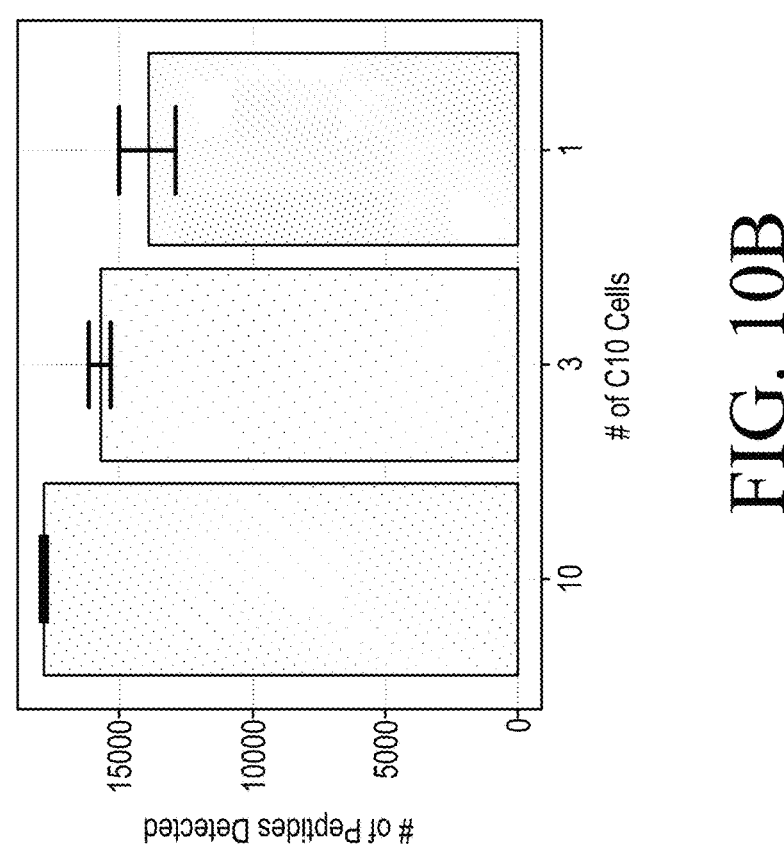
FIGS. 10A-10B are proteomics data when using methods to an embodiment of the disclosure.
Figure 10A:
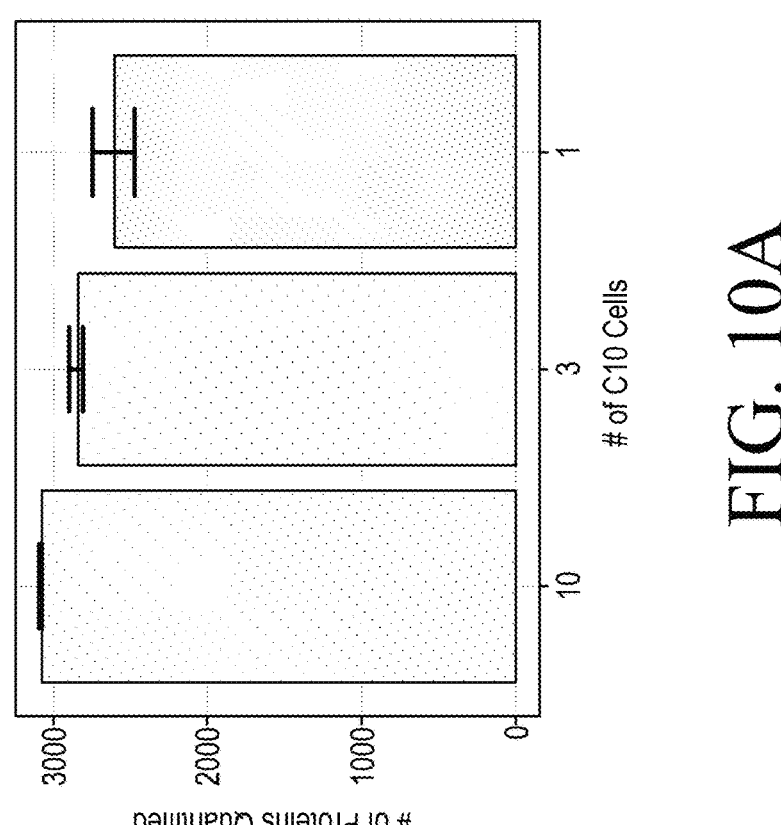
Figure 11:
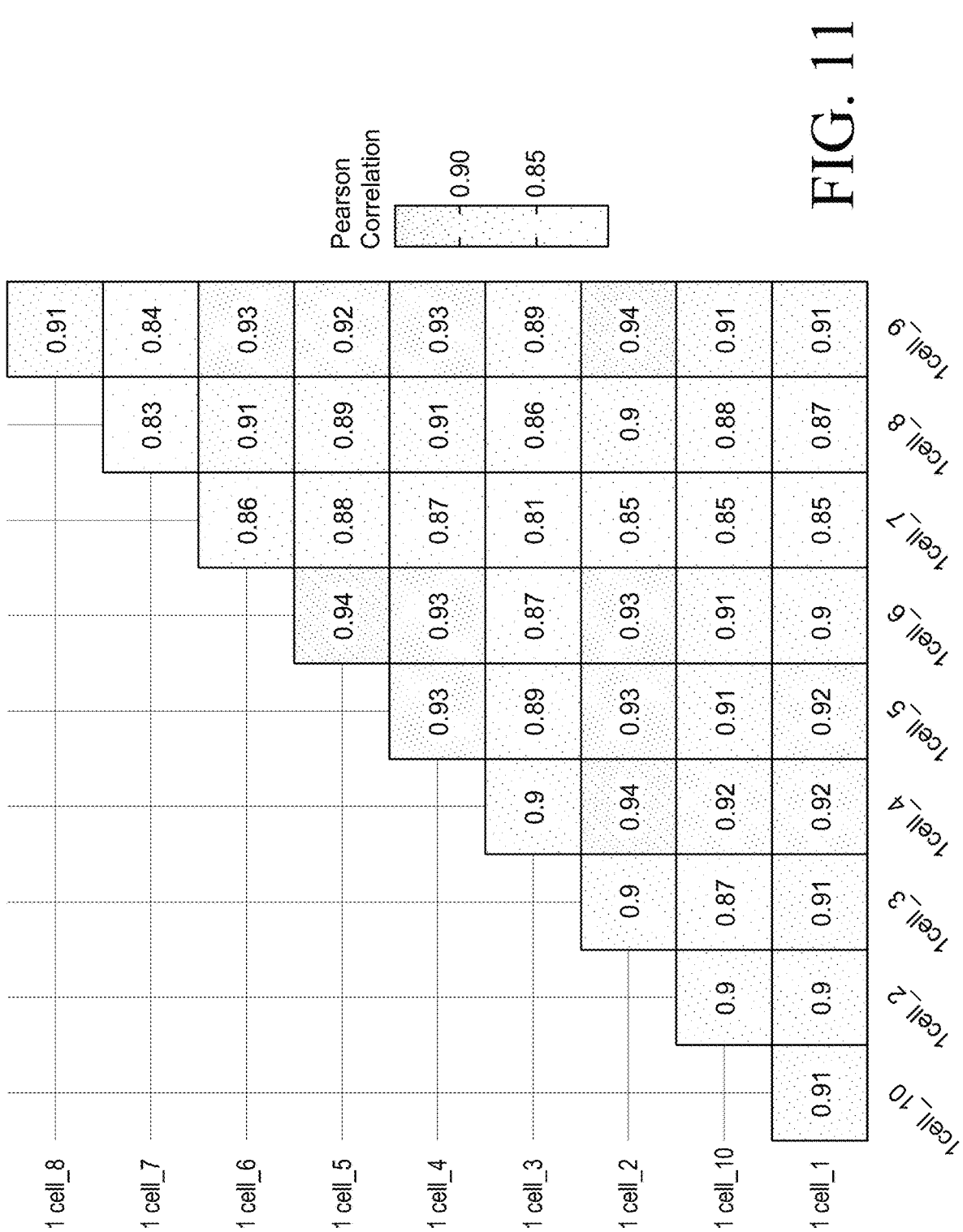
FIG. 11 depicts Pearson correlation of protein intensities (ten C10 cell, five replicates) when using methods according to an embodiment of the disclosure.
Figure 12:
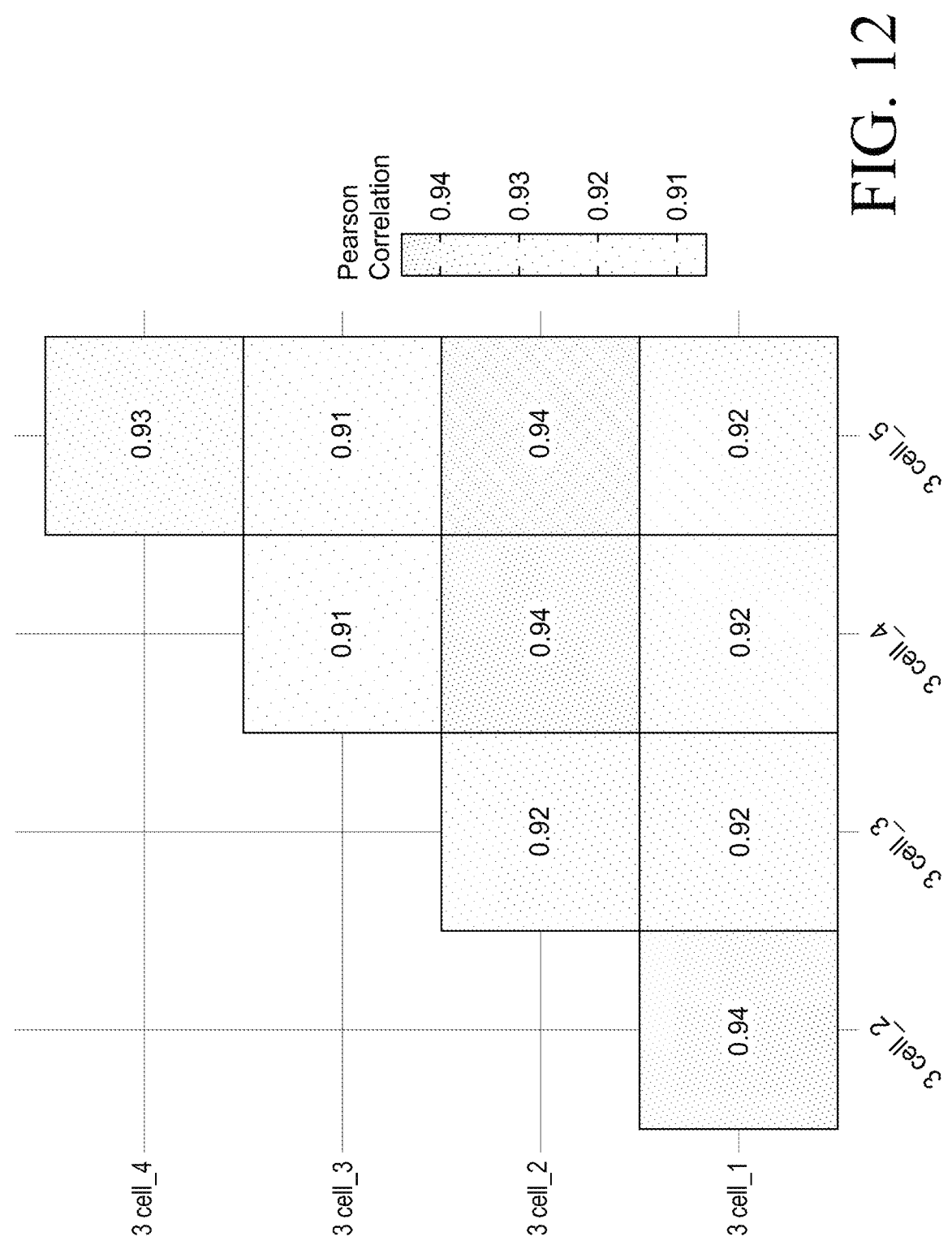
FIG. 12 depicts Pearson correlation of protein intensities (three C10 cell, five replicates) when using methods according to an embodiment of the disclosure.
Figure 13:
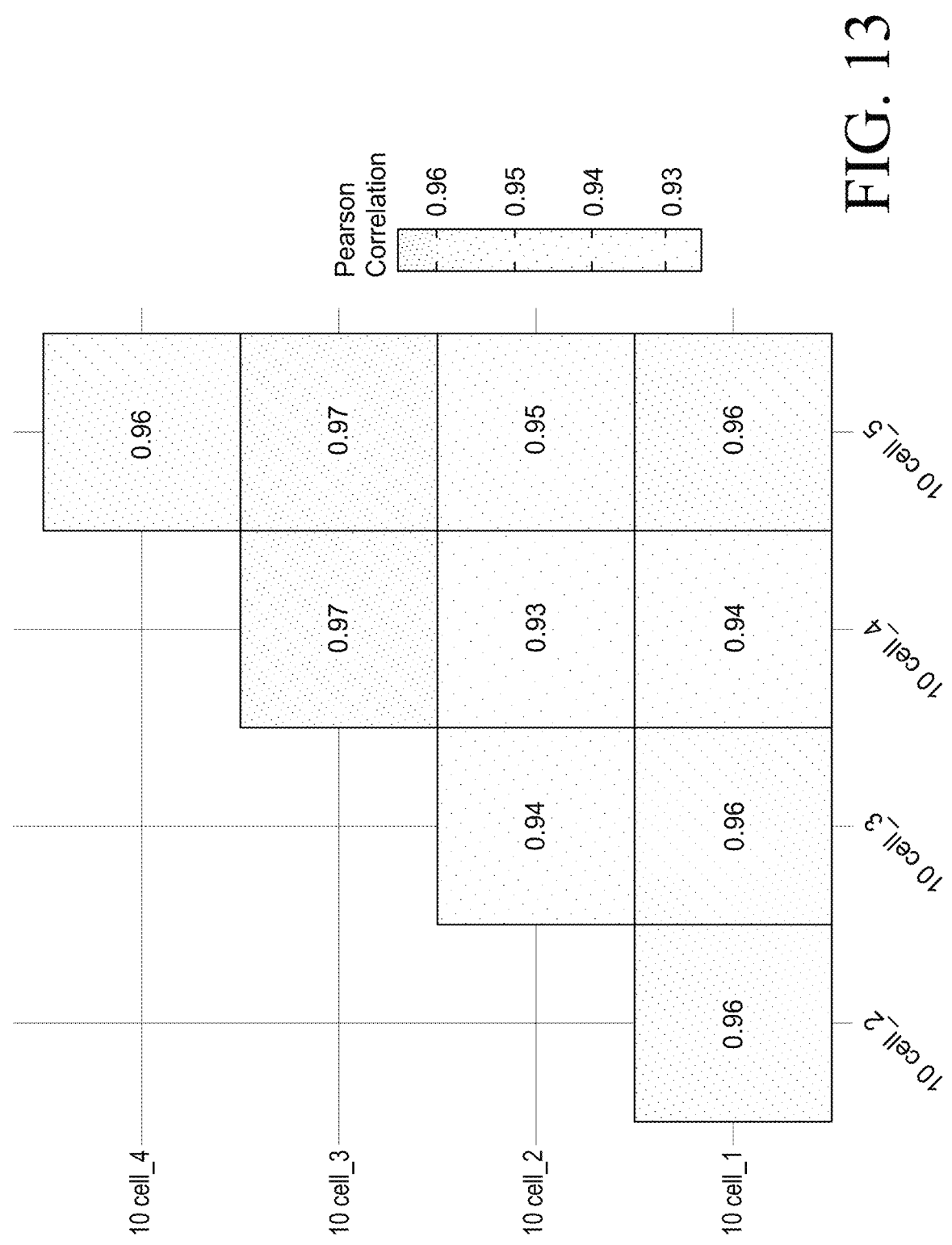
FIG. 13 depicts Pearson correlation of protein intensities (ten C10 cell, five replicates) when using methods according to an embodiment of the disclosure.
Figures 14, 15:
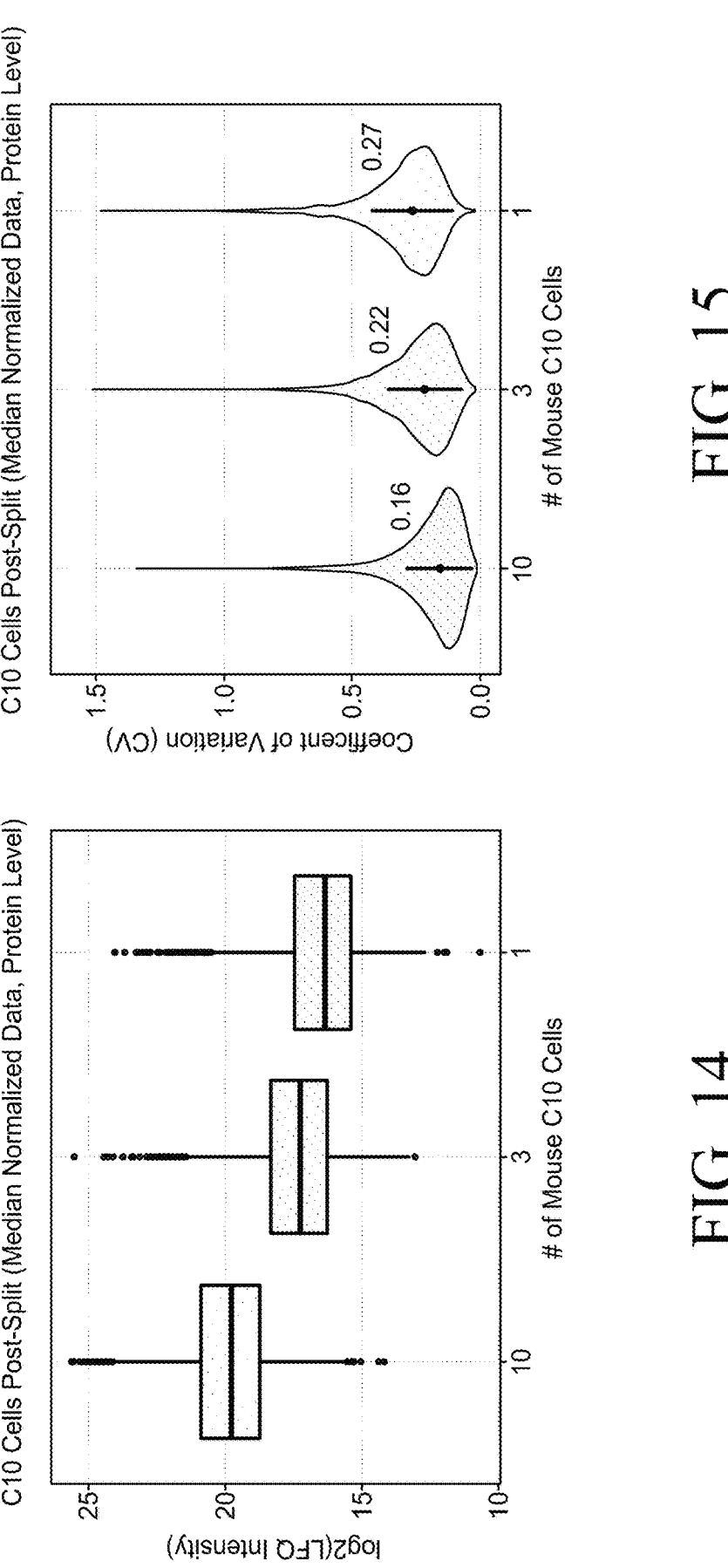
FIGS. 14-15 depict summed protein intensity distribution and CVs to show the high reproducibility of the methods according to embodiments of the disclosure.
Figure 16:
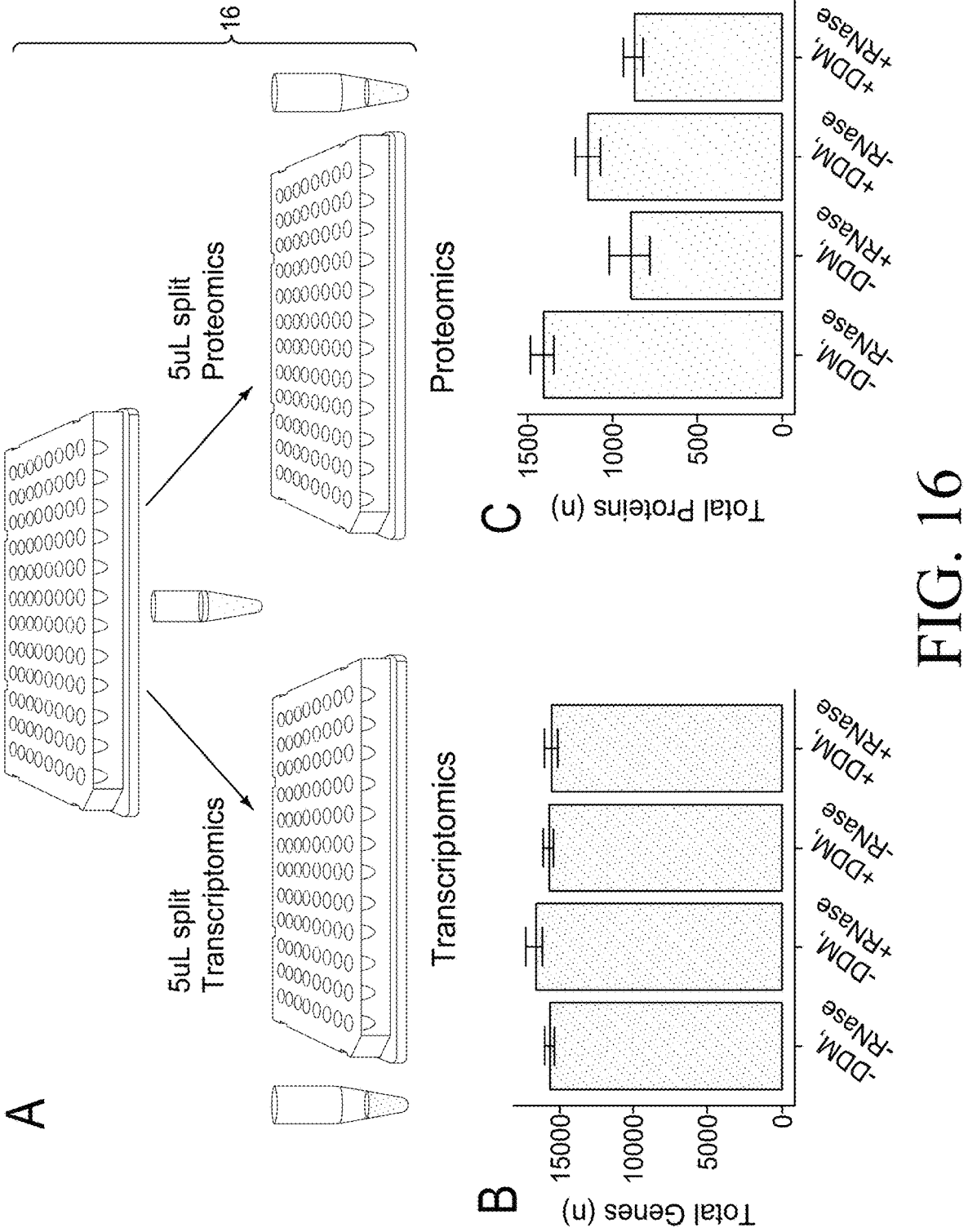
FIG. 16 is an overview of buffer optimization experiment using C10 cells in 96-well PCR plate when using methods according to an embodiment of the disclosure.

FIGS. 9A and 9B depict gel electrophoresis data to show the RNA presented in accepter droplet of both single and multicell analyses, showing successfully split cell lysate for transcriptomics and proteomics analyses. SMART-Seq V4 was used to generate full-length cDNA. FIGS. 10A-10B are proteomics data to show proteins detected in donor chips after splitting, indicating the average number of proteins and peptides quantified across 3 replicates. FIG. 11 shows Pearson correlation of protein intensities (single C10 cells, 10 replicates). FIG. 12 depicts Pearson correlation of protein intensities (three C10 cells, five replicates) according to an embodiment of the disclosure. FIG. 13 depicts Pearson correlation of protein intensities (ten C10 cells, five replicates) according to an embodiment of the disclosure. FIGS. 14-15 depict protein intensity distribution and CVs to show the high reproducibility of the method according to embodiments of the disclosure.

With respect to FIG. 16A, an overview of buffer analysis using C10 cells in 96-well PCR plate is shown (see below for methods and materials for buffer determination). 20 cells were sorted into each well and lysed with 10 μL of four different lysis buffers. 5 μL from each well was then transferred into a separate PCR plate for RNAseq analysis. FIG. 16B shows mean genes detected per condition with RNAseq and FIG. 16C shows mean proteins detected per condition with label-free proteomics. Error bars represent +/−sd. Conditions in FIG. 16B and FIG. 16C indicated by "+" or "−" represent the presence or absence of 0.1% DDM or 1×RNase inhibitor, respectively. Note the higher protein identifications in 10 mM Tris without DDM are due to more proteins being non-specifically bound to the PCR plate that was used in downstream proteomic sample processing.

Figure 17A:
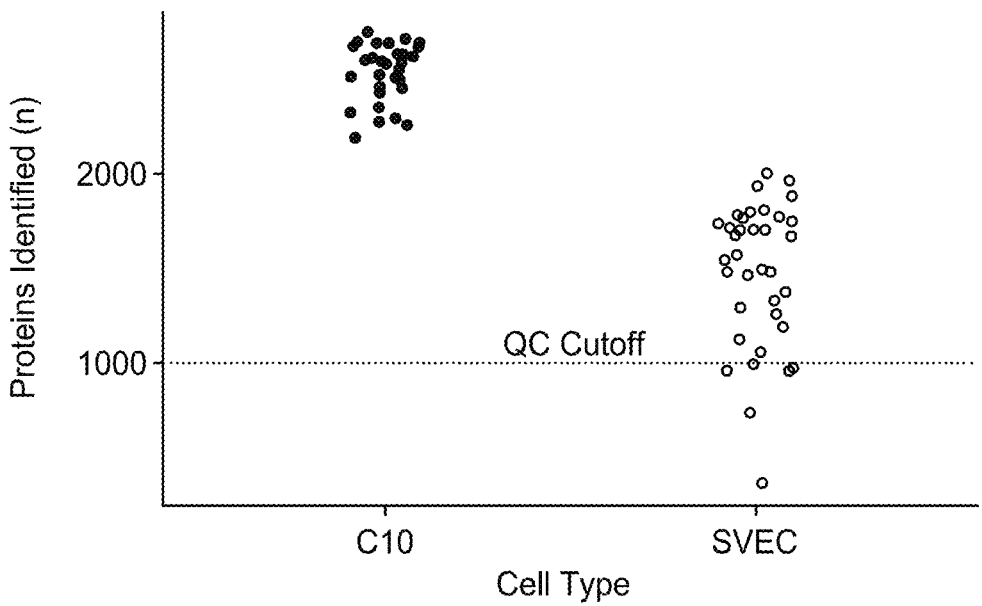
FIGS. 17A-17B depict total proteins identified per single C10 and SVEC cells using single-cell proteomics (scProteomics), and total genes identified per C10 and SVEC cells using scRNAseq when using methods according to embodiments of the disclosure.
Figure 17B:
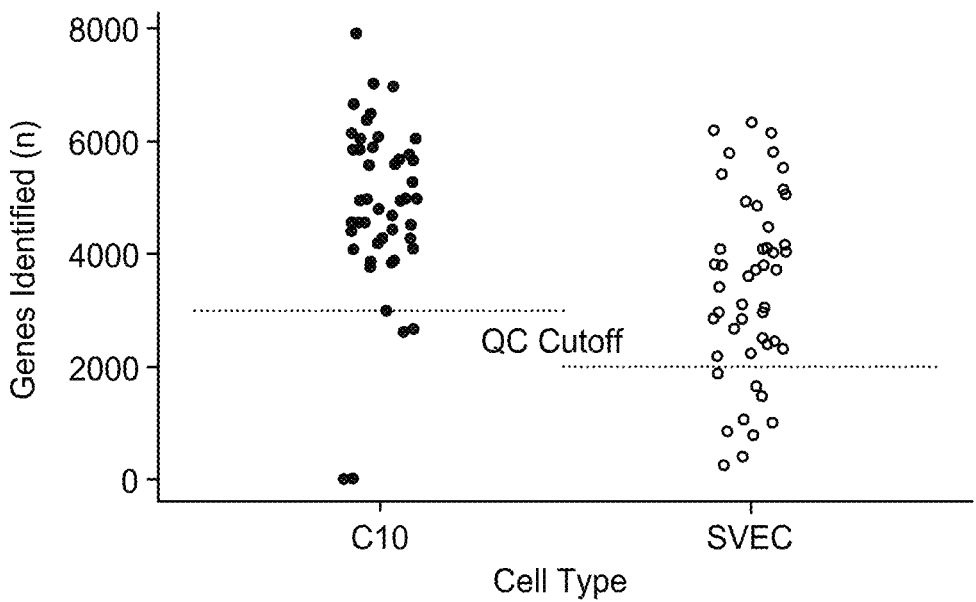

With respect to FIGS. 17A-17B, FIG. 17A shows total proteins identified per single C10 and SVEC cells using scProteomics. The dotted line indicates quality control cutoff for downstream analysis. FIG. 17B shows total genes identified per C10 and SVEC cells using scRNAseq. The dotted line indicates quality control cutoff for downstream analysis.

Figure 18A:
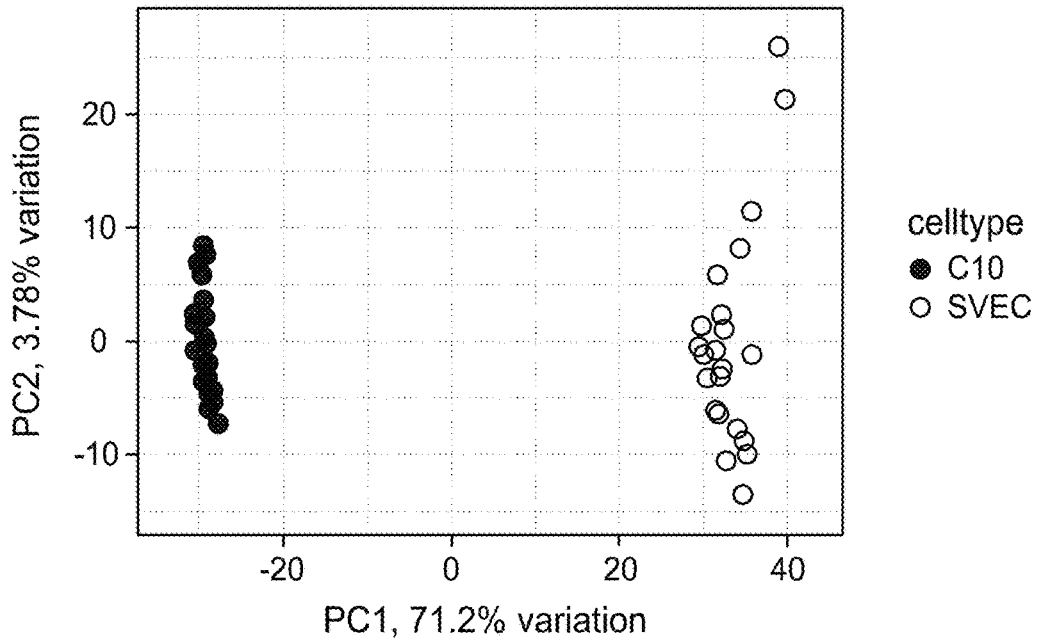
FIGS. 18A-18B show PCA of SVEC and C10 cells using scProteomics data and PCA of SVEC and C10 cells using scRNAseq data when using methods according to embodiments of the disclosure.
Figure 18B:
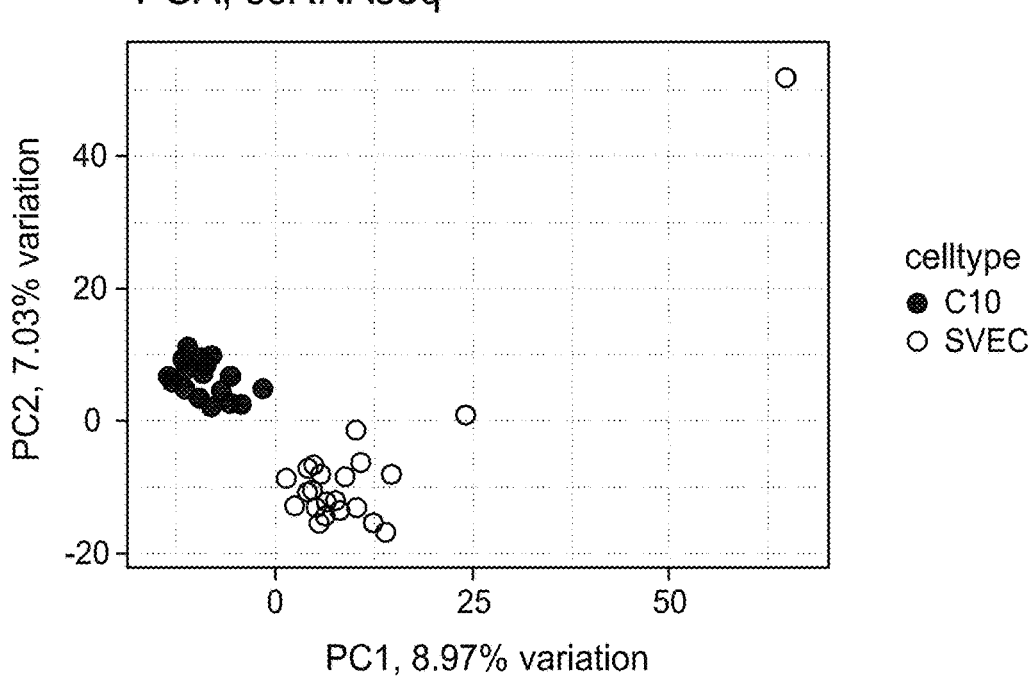

With respect to FIGS. 18A-18B, FIG. 18A shows PCA of SVEC and C10 cells using scProteomics data. FIG. 18B shows PCA of SVEC and C10 cells using scRNAseq data.

Figure 19:
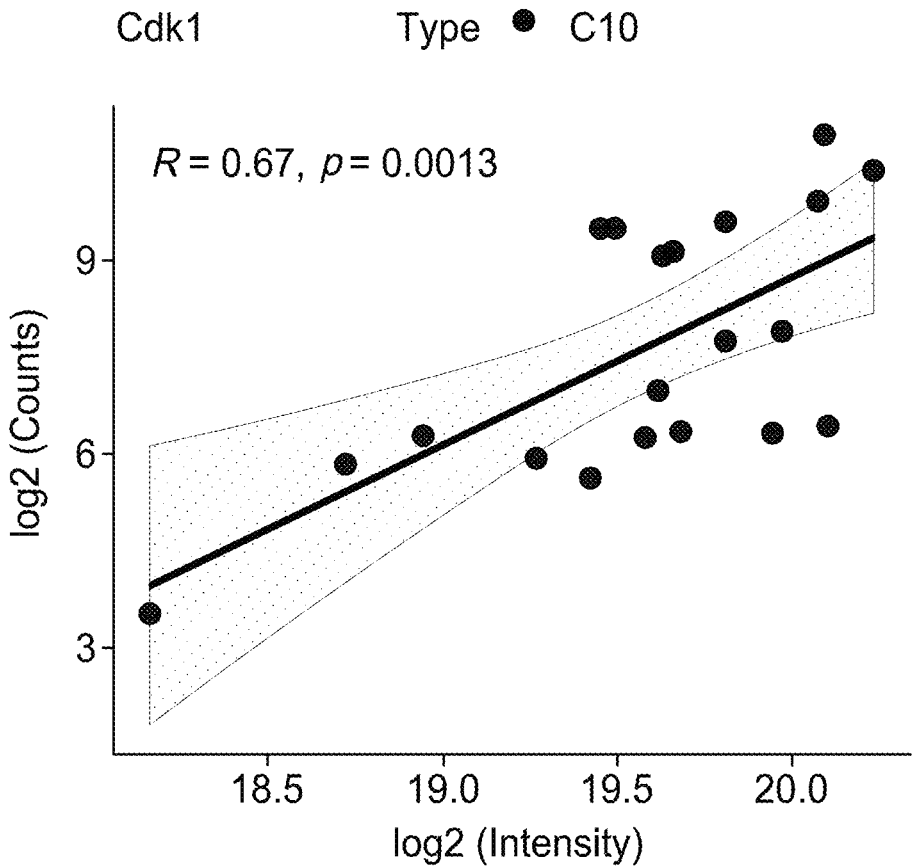
FIG. 19 is Pearson correlation based on linear regression between Cdk1 mRNA (counts) and protein (raw intensity) within C10 cells when using methods according to an embodiment of the disclosure.
Figure 20A:
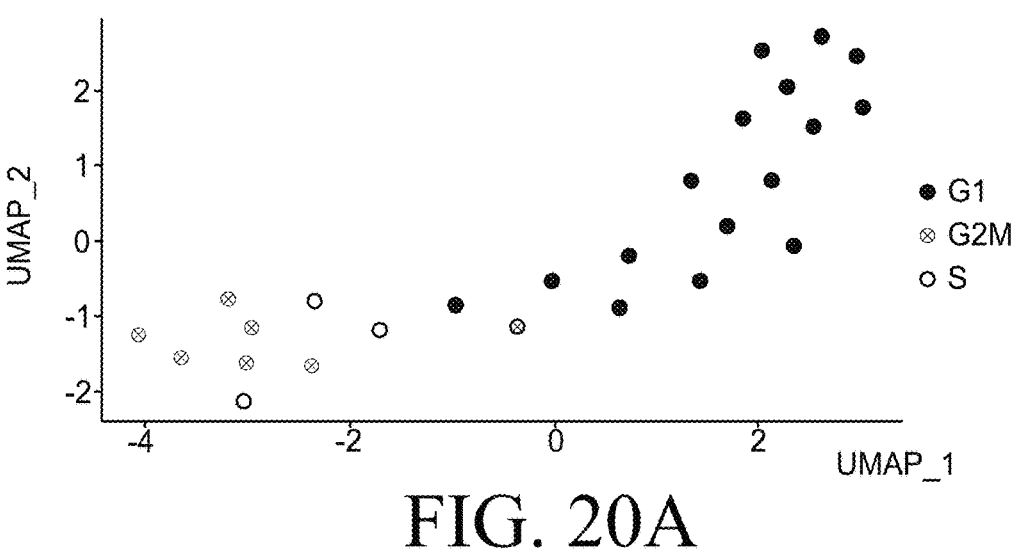
FIGS. 20A-20E are feature UMAPs generated using previously established cell-cycle features when using methods according to embodiments of the disclosure.
Figure 20B:
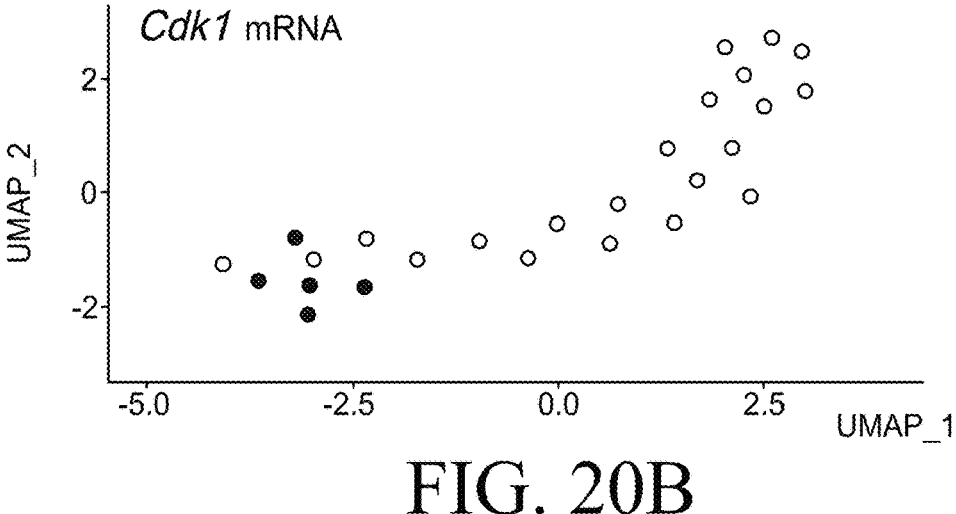
Figure 20C:
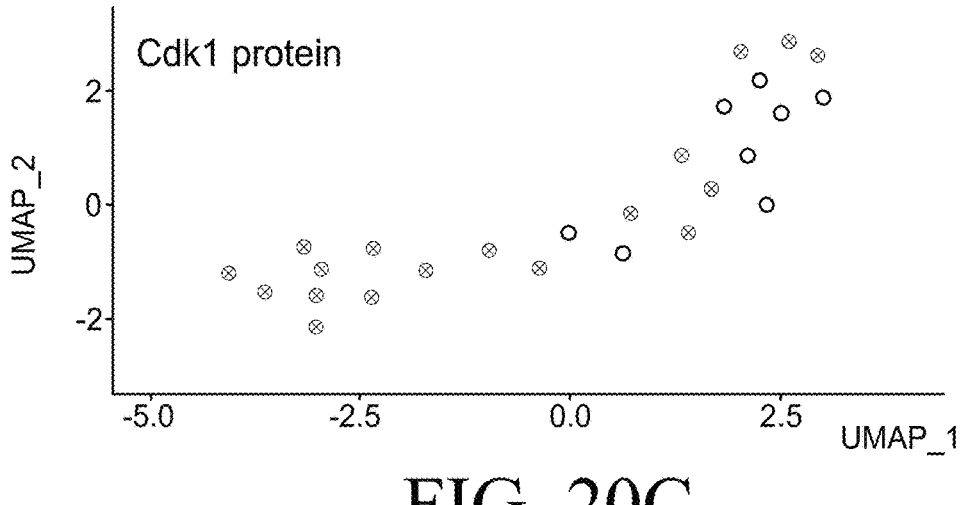
Figure 20D:
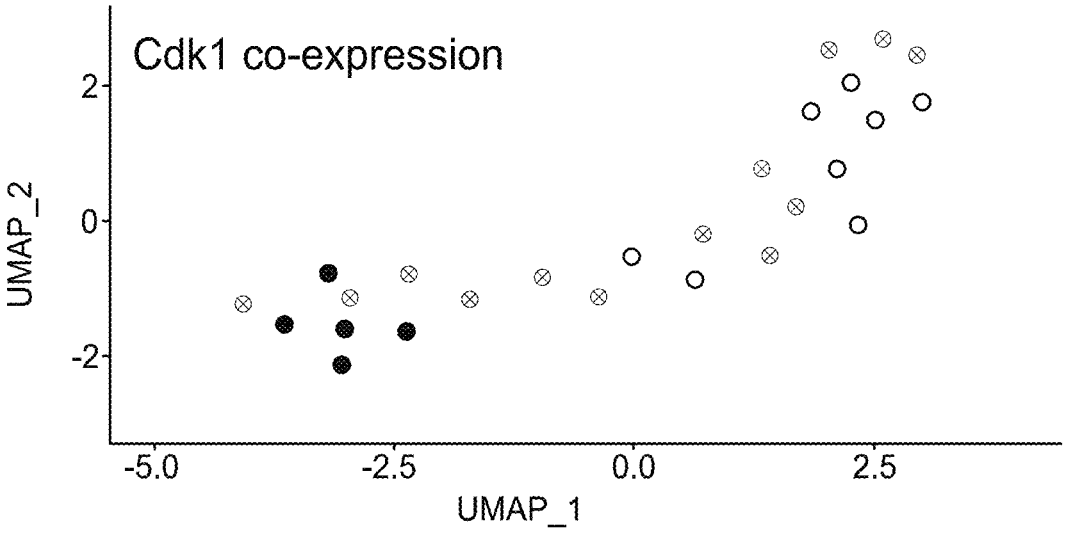
Figure 20E:
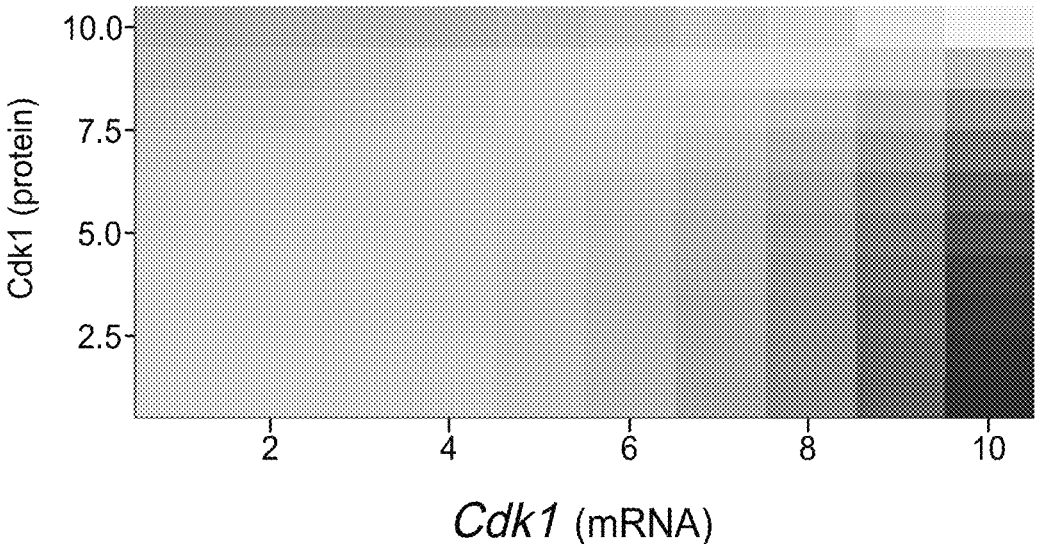

FIG. 19 shows Pearson correlation based on linear regression between Cdk1 mRNA (counts) and protein (raw intensity) within C10 cells. The shaded region represents 95% confidence intervals, and all values are log 2 transformed.

With respect to FIGS. 20A-20E, FIG. 20A is a feature UMAP generated using previously established cell-cycle features. FIGS. 20B-20E depict the same UMAP as FIG. 20A, but with relative abundances of Cdk1 mRNA (20B, G1), protein (20C, G2M), and both (20D) based on a co-expression map (20E). The upper right corner values indicate greater relative expression of both Cdk1 protein and mRNA, while the lower left corner indicates lower co-expression.

Buffer Analysis Methods and Materials.

Buffer analysis. Using nuclease-free water (Thermo Fisher Scientific, cat #4387936), 10 mM Tris pH 8 test buffers were created containing 0.1% DDM and/or 1×RNase inhibitor. 10 μL of each buffer was added to four wells within a 96 well plate. 20 C10 cells were then sorted into each well before snap freezing with liquid nitrogen. Immediately after thawing and centrifugation at 2,500 g, 5 μL from each well was transferred to a separate 96 well PCR plate containing 7.5 μL of 3' SMART-Seq CDS primer II before heating 70° C. for 3 min. 7.5 μL of RT mix (4 μL 5× ultra low first-strand buffer, 1 μL 48 μM SMART-Seq V4 oligonucleotide, 0.5 μL 40 units/μL RNase inhibitor, 2 μL SMARTScribe II reverse transcriptase) was then added before incubation at 42° C. for 90 min and 70° C. for 10 min. 30 μL of PCR master mix (25 μL SeqAmp PCR buffer, 1 μL PCR primer II A, 3 μL water, 1 μL SeqAmp DNA polymerase) was then added to each tube before performing 18 cycles of PCR (98° C. for 10 sec, 65° C. for 30 sec, 68° C. for 3 min). Isolation of cDNA was performed with Ampure XP beads with 80% ethanol washes. cDNA concentration and quality were determined with a Qubit fluorometer and Agilent fragment analyzer before next generation-sequencing, respectively.

The remaining 5 μL was retained and processed for label free proteomic analysis. Briefly, 5 μL of extraction buffer containing DTT and DDM was added to cell lysate to bring each sample to a final concentration of 1 mM DTT and 0.1%

DDM before incubation at 60° C. for 1 h. 2 μL of 12 mM IAA was then added for a final concentration of 2 mM IAA before a 30 min incubation at 37° C. 2 μL of 2.5 ng/μL Lys-C and 10 ng/μL of trypsin was added before incubation at 37° C. for 10 h. Enzymatic digestion was quenched by adding formic acid to a concentration of 1% before drying samples under vacuum. Peptides were reconstituted in 3 μL 5% acetonitrile 0.1% FA and proteomic analysis was performed.

In compliance with the statute, embodiments of the invention have been described in language more or less specific as to structural and methodical features. It is to be understood, however, that the entire invention is not limited to the specific features and/or embodiments shown and/or described, since the disclosed embodiments comprise forms of putting the invention into effect. The invention is, therefore, claimed in any of its forms or modifications within the proper scope of the appended claims appropriately interpreted in accordance with the doctrine of equivalents.

The invention claimed is:

1. A method of determining multiple omics of a single biological cell, the multiple omics including at least a first omics and a second omics, by performing in parallel multiple omics analyses on a plurality of droplets having cellular components originating from the single biological cell, the multiple omics analyses including at least a first omics analysis and a second omics analysis, the method comprising:

isolating a single biological cell by providing a cell isolation droplet having only a single biological cell;

providing a cell lysate droplet by lysing the isolated single biological cell in the cell isolation droplet;

preparing the plurality of droplets including at least a first droplet and a second droplet having the cellular components from the lysed isolated single biological cell by dividing the cell lysate droplet;

acquiring a first set of analytical data of the single biological cell by performing the first omics analysis on the first droplet using a first plurality of analytical techniques;

acquiring a second set of analytical data of the single biological cell by performing the second omics analysis on the second droplet using a second plurality of analytical techniques, wherein the first plurality of analytical techniques is different from the second plurality of analytical techniques and the first set of analytical data is different from the second set of analytical data; and determining the first omics of the lysed isolated single biological cell by processing the first set of analytical data and determining the second omics of the lysed isolated single biological cell by processing the second set of analytical data.

2. The method of claim 1 wherein the first omics analysis or the second omics analysis comprises mRNA analysis, DNA analysis, protein analysis, lipid analysis, metabolite analysis, and phenotype analysis, or a combination thereof.

3. The method of claim 1 wherein the first omics analysis or the second omics analysis comprises one or more sequencing strategies.

4. The method of claim 3 wherein the one or more sequencing strategies comprise DNA sequencing, DNA methylation sequencing, and chromatin accessibility profiling, or a combination thereof.

5. The method of claim 1 wherein the first omics analysis or the second omics analysis comprises mass spectrometry analysis.

6. The method of claim 1 wherein the first omics analysis comprises single-cell proteomics and the second omics analysis comprises single-cell RNA sequencing.

* * * * *